US010856761B2

(12) United States Patent
Malhotra et al.

(10) Patent No.: US 10,856,761 B2
(45) Date of Patent: Dec. 8, 2020

(54) METHOD AND SYSTEM TO DETECT P-WAVES IN CARDIAC ARRHYTHMIC PATTERNS

(71) Applicant: PACESETTER, INC., Sylmar, CA (US)

(72) Inventors: Neha Malhotra, Los Angeles, CA (US); Fujian Qu, San Jose, CA (US); Jong Gill, Valencia, CA (US); Stuart Rosenberg, Castaic, CA (US); Gene A. Bornzin, Simi Valley, CA (US); Fady Dawoud, Santa Clara, CA (US)

(73) Assignee: Pacesetter, Inc., Sylmar, CA (US)

( * ) Notice: Subject to any disclaimer, the term of this patent is extended or adjusted under 35 U.S.C. 154(b) by 190 days.

(21) Appl. No.: 15/973,107

(22) Filed: May 7, 2018

(65) Prior Publication Data
US 2019/0336031 A1    Nov. 7, 2019

(51) Int. Cl.
*A61B 5/04* (2006.01)
*A61B 5/0452* (2006.01)
(Continued)

(52) U.S. Cl.
CPC ........ *A61B 5/04525* (2013.01); *A61B 5/0245* (2013.01); *A61B 5/02405* (2013.01);
(Continued)

(58) Field of Classification Search
CPC . A61B 5/04525; A61B 5/7221; A61B 5/0468; A61B 5/046; A61B 5/0456;
(Continued)

(56) References Cited

U.S. PATENT DOCUMENTS 3,946,744 A    3/1976 Auerbach
5,713,367 A    2/1998 Arnold et al.
(Continued)

OTHER PUBLICATIONS

Extended European Search Report for corresponding EP Application No. 19172674.4 dated Oct. 4, 2019 (8 pages).
(Continued)

*Primary Examiner* — Amanda K Hulbert
*Assistant Examiner* — Natasha Patel
(74) *Attorney, Agent, or Firm* — The Small Patent Law Group LLC; Dean D. Small

(57) ABSTRACT

Methods and systems are provided for detecting arrhythmias in cardiac activity. The methods and systems declare a current beat, from the CA signals, to be a candidate beat or an ineligible beat based on whether the current beat satisfies the rate based selection criteria. The determining and declaring operations are repeated for multiple beats to form an ensemble of candidate beats. The method and system calculate a P-wave segment ensemble from the ensemble of candidate beats, perform a morphology-based comparison between the P-wave segment ensemble and at least one of a monophasic or biphasic template, declare a valid P-wave to be present within the CA signals based on the morphology-based comparison, and utilize the valid P-wave in an arrhythmia detection process to determine at least one of an arrhythmia entry, arrhythmia presence or arrhythmia exit.

20 Claims, 12 Drawing Sheets

(51) Int. Cl.

| | | |
|---|---|---|
| *A61B 5/024* | (2006.01) | |
| *A61B 5/0245* | (2006.01) | |
| *A61B 5/0456* | (2006.01) | |
| *A61B 5/046* | (2006.01) | |
| *A61B 5/0468* | (2006.01) | |
| *A61B 5/00* | (2006.01) | |

(52) U.S. Cl.
CPC .......... *A61B 5/046* (2013.01); *A61B 5/04012* (2013.01); *A61B 5/0456* (2013.01); *A61B 5/0468* (2013.01); *A61B 5/7221* (2013.01)

(58) Field of Classification Search
CPC .............. A61B 5/04012; A61B 5/0245; A61B 5/02405; A61N 1/37211; A61N 1/3956; A61N 1/36507
See application file for complete search history.

(56) References Cited

U.S. PATENT DOCUMENTS

| | | |
|---|---|---|
| 7,248,921 B2 | 7/2007 | Palreddy et al. |
| 7,294,108 B1 | 11/2007 | Bomzin et al. |
| 7,894,894 B2 | 2/2011 | Stadler et al. |
| 8,135,456 B2 | 3/2012 | Haluska |
| 8,260,404 B1 | 9/2012 | Bharmi et al. |
| 8,332,022 B2 | 12/2012 | Brown et al. |
| 8,391,980 B2 | 3/2013 | Bomzin et al. |
| 8,831,713 B2 | 9/2014 | Stadler et al. |
| 8,831,747 B1 | 9/2014 | Min et al. |
| 9,044,610 B2 | 6/2015 | Rosenberg et al. |
| 9,174,062 B2 | 11/2015 | Stadler et al. |
| 9,216,285 B1 | 12/2015 | Boling et al. |
| 9,232,485 B2 | 1/2016 | Wu et al. |
| 9,333,351 B2 | 5/2016 | Arnold et al. |
| 9,486,155 B2 | 11/2016 | Sarkar et al. |
| 2006/0235476 A1 | 10/2006 | Gunderson et al. |
| 2008/0082014 A1 | 4/2008 | Cao et al. |
| 2009/0270749 A1* | 10/2009 | Haluska ................. A61B 5/046 600/518 |
| 2009/0281587 A1* | 11/2009 | Pei ..................... A61B 5/04525 607/9 |
| 2011/0125206 A1* | 5/2011 | Bornzin ............... A61N 1/3956 607/5 |
| 2012/0029373 A1 | 2/2012 | Stadler et al. |
| 2013/0138005 A1 | 5/2013 | Dong et al. |
| 2015/0038863 A1* | 2/2015 | Schotten ............ A61B 5/04525 600/509 |
| 2016/0213270 A1 | 7/2016 | Cao et al. |
| 2017/0251940 A1 | 9/2017 | Perschbacher et al. |
| 2017/0273589 A1 | 9/2017 | Sarkar et al. |
| 2018/0064360 A1 | 3/2018 | Siejko et al. |

OTHER PUBLICATIONS

Extended European Search Report for corresponding EP Application No. 19172673.6 dated Jul. 15, 2019 (5 pages).

* cited by examiner

METHOD AND SYSTEM TO DETECT P-WAVES IN CARDIAC ARRHYTHMIC PATTERNS

RELATED APPLICATIONS

The following applications relate to and are filed concurrently on the same day as the present application, and are expressly incorporated herein by reference in their entireties (hereafter referred to as "Co-Pending Related Applications"):

U.S. patent application Ser. No. 14/973,126, filed 7 May 2018 (now U.S. Pat. No. 10,729,346 issued 4 Aug. 2020), titled "METHOD AND SYSTEM FOR SECOND PASS CONFIRMATION OF DETECTED CARDIAC ARRHYTHMIC PATTERNS", U.S. patent application Ser. No. 15/973,351, filed 7 May 2018, titled "METHOD AND SYSTEM TO DETECT R-WAVES IN CARDIAC ARRHYTHMIC PATTERNS", U.S. patent application Ser. No. 15/973,307, filed 7 May 2018, titled "METHOD AND SYSTEM TO DETECT POST VENTRICULAR CONTRACTIONS IN CARDIAC ARRHYTHMIC PATTERNS", and U.S. Patent Application No. 62/668,093, filed 7 May 2018, titled "METHOD AND SYSTEM TO DETECT NOISE IN CARDIAC ARRHYTHMIC PATTERNS".

FIELD OF THE INVENTION

Embodiments herein relate generally to implantable medical devices, and more particularly to detection and discrimination of an underlying arrhythmic events based on P-waves.

BACKGROUND OF THE INVENTION

Today, numerous atrial fibrillation (AF) detection processes are implemented within implantable cardiac monitors (ICMs) that detect atrial fibrillation based on irregularities and variation patterns in RR intervals. In some embodiments, the AF detection process steps beat by beat through cardiac activity (CA) signals and analyzes the RR intervals over a period of time. An AF detection is declared when the RR interval pattern for the suspect beat segments is sufficiently dissimilar from RR interval patterns for sinus beat segments.

However, AF detection processes may exhibit false AF detection where the ICM provides a device documented AF episode, even though a patient is not experiencing AF. False AF detection may arise due to various conditions and behavior of the heart, such as when a patient experiences sick sinus rhythms with irregular RR intervals, experiences frequent premature ventricular contractions (PVCs) and/or inappropriate R-wave sensing. To an extent, false AF detection is due, in part, to dependence of the AF detection process upon identification of R-wave features, with the or no input concerning other features of a cardiac event.

SUMMARY

In accordance with embodiments herein, a reliable P-wave detection process is provided to accurately detect P-waves, even though P-wave exhibits relatively small amplitude as compared to other morphology features of a cardiac event such as QRS complex and T wave, P-waves still remain present during sick sinus rhythm but not during AF. In accordance with embodiments herein, accurate P-wave detection may be utilized to improve specificity of an AF detection process, such as in an ICM.

In accordance with embodiments herein, a P-wave detection process is described for use with improved AF detection. Given that an amplitude of a P-wave is relatively small within an EGM signal and subject to noise, as well as beat by beat variation, embodiments herein utilize advanced signal processing techniques to accurately detect the presence of P-waves and to confirm the P-waves utilizing morphology based template matching.

In accordance with embodiments herein, a computer implemented method is provided for detecting arrhythmias in cardiac activity. The method comprises, under control of one or more processors configured with specific executable instructions, obtaining a far field cardiac activity (CA) data set that includes far field CA signals for a series of beats, determining whether the current beat satisfies a rate based selection criteria, declaring a current beat, from the CA signals, to be a candidate beat or an ineligible beat based on whether the current beat satisfies the rate based selection criteria, and repeating the determining and declaring operations for multiple beats to form an ensemble of candidate beats. The method also comprises calculating a P-wave segment ensemble from the ensemble of candidate beats, performing a morphology-based comparison between the P-wave segment ensemble and at least one of a monophasic or biphasic template, declaring a valid P-wave to be present within the CA signals based on the morphology-based comparison, and utilizing the valid P-wave in an arrhythmia detection process to determine at least one of an arrhythmia entry, arrhythmia presence or arrhythmia exit.

Additionally or alternatively, the rate based selection criteria represents a RR interval rate criteria in which a beat is disregard when the RR interval is outside of a predetermined range. Additionally or alternatively, the determining operation comprises applying a two-part selection test that includes i) determining whether an RR interval of the current beat is within a predetermined range and ii) determining whether the current beat is greater or shorter than a previous beat, and if shorter, determining whether the current beat has a duration that is within a range of the previous beat. Additionally or alternatively, the method further comprises overlaying a P-wave search window onto a candidate segment within corresponding candidate beats to obtain candidate P-wave segments, combining the candidate P-wave segments to form a P-wave combination, and determining whether a signal characteristic of interest from the P-wave combination exceeds one or more P-wave limits. Additionally or alternatively, the method further comprises truncating the candidate P-wave segments when the signal characteristic of the P-wave combination exceeds the one or more P-wave limits, the calculating operation calculating the final P-wave segment ensemble based on the candidate P-wave segments after truncation. Additionally or alternatively, the method further comprises de-trending the ensemble of candidate beats to remove baseline drift from individual P-wave segments for corresponding candidate beats.

Additionally or alternatively, the method further comprises normalizing the P-wave segment ensemble before performing the correlating operation. Additionally or alternatively, the method further comprises correlating a first P-wave segment, for a first beat from the ensemble of candidate beats, with the P-wave segment ensemble for the ensemble of candidate beats for morphology similarity analysis. Additionally or alternatively, the declaring operation further comprises declaring the valid P-wave to be present within the CA signals when the correlation between the P-wave segment ensemble and at least one of the monophasic or biphasic template satisfies a correlation threshold. Additionally or alternatively, the declaring operation further comprises declaring the P-wave segment ensemble to not include a P-wave when the correlation between the P-wave segment ensemble and both of the monophasic and biphasic templates do not satisfy a correlation threshold.

In accordance with embodiments herein a system is provided for detecting arrhythmias in cardiac activity. The system comprises memory to store specific executable instructions; and one or more processors configured to execute the specific executable instructions for: obtaining a far field cardiac activity (CA) data set that includes far field CA signals for a series of beats, determining whether the current beat satisfies a rate based selection criteria, declaring a current beat, from the CA signals, to be a candidate beat or an ineligible beat based on whether the current beat satisfies the rate based selection criteria, repeating the determining and declaring operations for multiple beats to form an ensemble of candidate beats, calculating a P-wave segment ensemble from the ensemble of candidate beats, performing a morphology-based comparison between the P-wave segment ensemble and at least one of a monophasic or biphasic template, declaring a valid P-wave to be present within the CA signals based on the morphology-based comparison, and utilizing the valid P-wave in an arrhythmia detection process to determine at least one of an arrhythmia entry, arrhythmia presence or arrhythmia exit.

Additionally or alternatively, the rate based selection criteria represents a RR interval rate criteria in which a beat is disregard when the RR interval is outside of a predetermined range. Additionally or alternatively, the one or more processors are configured to perform the determining operation by applying a two-part selection test that includes i) determining whether an RR interval of the current beat is within a predetermined range and ii) determining whether the current beat is greater or shorter than a previous beat, and if shorter, determining whether the current beat has a duration that is within a range of the previous beat. Additionally or alternatively, the one or more processors are configured to further: overlay a P-wave search window onto a candidate segment within corresponding candidate beats to obtain candidate P-wave segments, combine the candidate P-wave segments to form a P-wave combination, and determine whether a signal characteristic of interest from the P-wave combination exceeds one or more P-wave limits.

Additionally or alternatively, the one or more processors are configured to truncate the candidate P-wave segments when the signal characteristic of the P-wave combination exceeds the one or more P-wave limits, the calculating operation calculating the final P-wave segment ensemble based on the candidate P-wave segments after truncation. Additionally or alternatively, the one or more processors are configured to de-trend the ensemble of candidate beats to remove baseline drift from individual P-wave segments for corresponding candidate beats. Additionally or alternatively, the one or more processors are configured to normalize the P-wave segment ensemble before performing the correlating operation. Additionally or alternatively, the one or more processors are configured to correlate a first P-wave segment, for a first beat from the ensemble of candidate beats, with the P-wave segment ensemble for the ensemble of candidate beats for morphology similarity analysis. Additionally or alternatively, the one or more processors are configured to declare the valid P-wave to be present within the CA signals when the correlation between the P-wave segment ensemble and at least one of the monophasic or biphasic template satisfies a correlation threshold. Additionally or alternatively, the one or more processors are configured to declare the P-wave segment ensemble to not include a P-wave when the correlation between the P-wave segment ensemble and both of the monophasic and biphasic templates do not satisfy a correlation threshold.

DETAILED DESCRIPTION

I. Terms and Abbreviations

Figure 1:
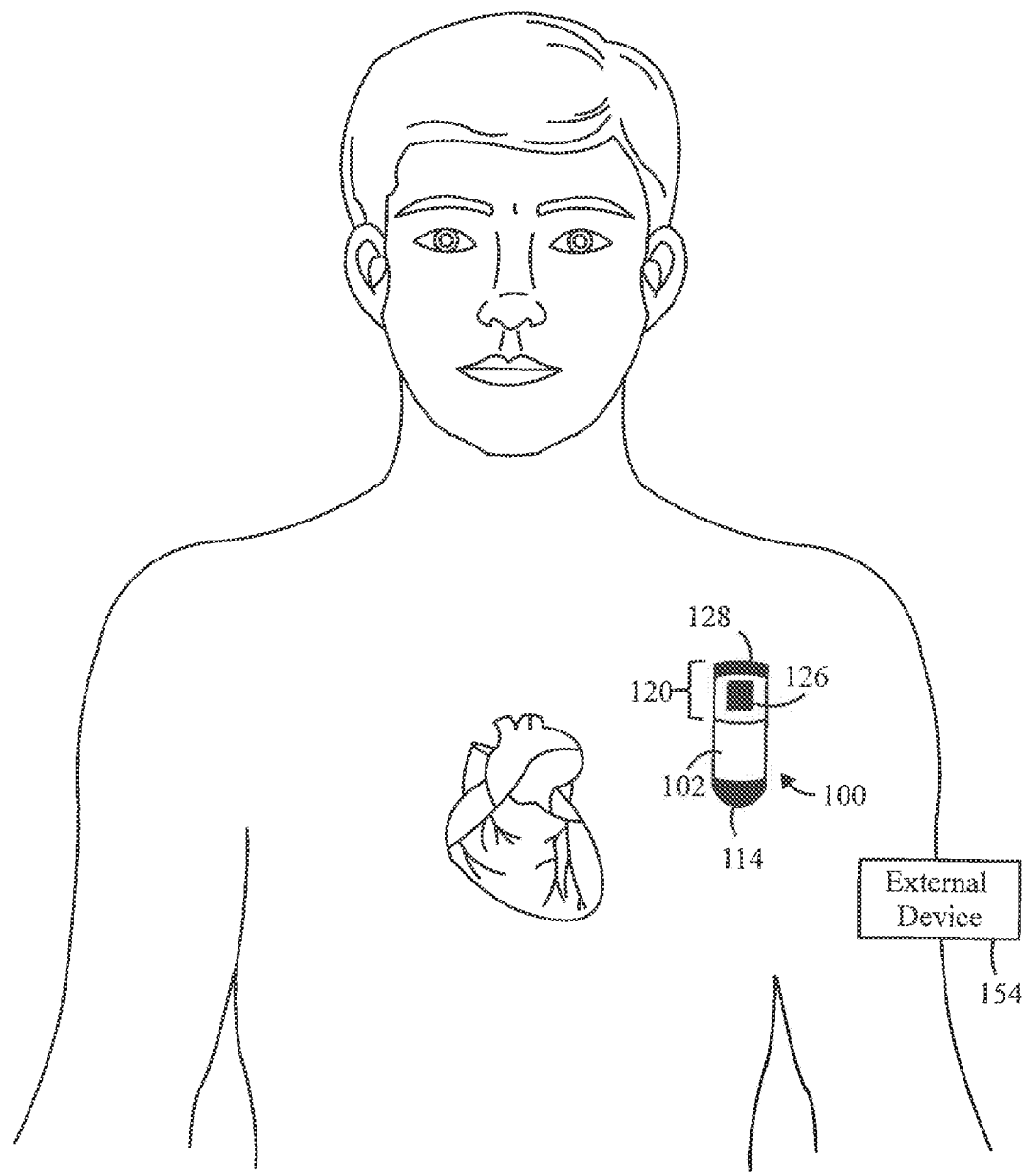
FIG. 1 illustrates an implantable cardiac monitoring device (ICM) intended for subcutaneous implantation at a site near the heart in accordance with embodiments herein.

The terms "cardiac activity signal", "cardiac activity signals", "CA signal" and "CA signals" (collectively "CA signals") are used interchangeably throughout to refer to an analog or digital electrical signal recorded by two or more electrodes positioned subcutaneous or cutaneous, where the electrical signals are indicative of cardiac electrical activity. The cardiac activity may be normal/healthy or abnormal/ arrhythmic. Non-limiting examples of CA signals include ECG signals collected by cutaneous electrodes, and EGM signals collected by subcutaneous electrodes.

The terms "cardiac activity data set" and "CA data set" (collectively "CA data set") are used interchangeably to refer to a data set that includes measured CA signals for a series of cardiac events in combination with device documented markers.

The term "marker" refers to data and/or information identified from CA signals that may be presented as graphical and/or numeric indicia indicative of one or more features within the CA signals and/or indicative of one or more episodes exhibited by the cardiac events. Markers may be superimposed upon CA signals or presented proximate to, and temporally aligned with, CA signals. Non-limiting examples of markers may include R-wave markers, noise markers, activity markers, interval markers, refractory markers, P-wave markers, T-wave markers, PVC markers, sinus rhythm markers, AF markers and other arrhythmia markers. As a further non-limiting example, basic event markers may include "AF entry" to indicate a beginning of an AF event, "in AF" to indicate that AF is ongoing, "AF exit" to indicate that AF has terminated, "T" to indicate a tachycardia beat, "B" to indicate a bradycardia beat, "A" to indicate an asystole beat, "VS" to indicate a regular sinus beat, "Tachy" to indicate a tachycardia episode, "Brady" to indicate a Bradycardia episode, "Asystole" to indicate an asystole episode, "Patient activated" to indicate a patient activated episode. An activity marker may indicate activity detected by activity sensor during the CA signal. Noise markers may indicate entry/start, ongoing, recovery and exit/stop of noise. Markers may be presented as symbols, dashed lines, numeric values, thickened portions of a waveform, and the like. Markers may represent events, intervals, refractory periods, ICM activity, and other algorithm related activity. For example, interval markers, such as the R-R interval, may include a numeric value indicating the duration of the interval. The AF markers indicate atrial fibrillation rhythmic.

The term "device documented marker" refers to markers that are declared by an implantable cardiac monitor and/or implantable medical device. Any or all of the foregoing examples of markers represent device document markers. Markers may be declared based on numerous criteria, such as signal processing, feature detection and AF detection software and hardware within and/or operating on the implantable cardiac monitor and/or implantable medical device.

The term "FOI" refers to a feature of interest within CA signals. Non-limiting examples of features of interest include an R-wave, P-wave, T-wave and isoelectric segments. A feature of interest may correspond to a peak of an individual R-wave, an average or median P, R or T-wave peak and the like.

The terms "beat" and "cardiac event" are used interchangeably and refer to both normal or abnormal events.

The terms "normal" and "sinus" are used to refer to events, features, and characteristics of, or appropriate to, a heart's healthy or normal functioning.

The terms "abnormal," or "arrhythmic" are used to refer to events, features, and characteristics of, or appropriate to, a un-healthy or abnormal functioning of the heart.

The term "real-time" refers to a time frame contemporaneous with a normal or abnormal episode occurrences. For example, a real-time process or operation would occur during or immediately after (e.g., within minutes or seconds after) a cardiac event, a series of cardiac events, an arrhythmia episode, and the like.

The term "adaptive", as used in connection with a sensitivity profile, sensitivity limit, sensitivity level or other sensing parameters, refers to an ability of the processes herein to modify the value of sensitivity and/or sensing parameters based on features within the CA signals. The sensitivity profile parameters may include refractory period, start sensitivity, decay delay, sensitivity limit, slope of sensitivity decay, etc.

The term "sensitivity level", as used herein, refers to a threshold that an input CA signal must exceed for an implantable device to identify a QRS complex feature of interest (e.g., an R-wave). As one non-limiting example, software may be implemented using a programmed sensitivity level to declare an R-wave to be detected when the input CA signal exceeds the current programmed sensitivity level In response, the software declares a device documented feature (e.g., R-wave) marker. The sensitivity level may be defined in various manners based on the nature of the CA signals. For example, when the CA signals measure electrical activity in terms of millivolts, the sensitivity level represents a millivolt threshold. For example, when a cardiac beat with a 0.14 mV amplitude is sensed by a device hardware, and R-wave may be detected when the current sensitivity level is programmed to 0.1 mV. However, when the sensitivity level is programmed to 0.15 mV or above, a cardiac beat with an amplitude of 0.14 mV will not be detected as an R-wave. Embodiments herein determine an adaptive sensitivity limit and sensitivity profile for the sensitivity level.

The term "turn", as used herein to refer to characteristics of a shape or morphology of a CA signal, shall mean changes in a direction of the CA signal. For example, the CA signal may turn by changing direction from a signal having a positive slope to a negative slope, or from a signal having a negative slope to a positive slope. Turns may have various associated characteristics such as amplitude, frequency (e.g., number of turns per unit time) and duration (e.g., an amount of time for the signal to exceed and drop below a desired percentage of the signal peak).

The terms "significant" and "non-significant", when used in connection with describing PVC burden, refer to an amount of PVC burden that is, or is not, sufficient to cause an AF detection algorithm to declare a false arrhythmia episode. A small number of PVC events, and/or a collection of PVC events that are spaced substantially apart from one another over time, may not be sufficient to be considered "significant" as the PVC events do not cause the AF detection algorithm to declare a false arrhythmia episode. Alternatively, when a sufficient number of PVC events occur within a relatively short period of time, the potential exists that the AF detection algorithm incorrectly identifies R-waves within the PVC events, leading to a declaration of a false arrhythmia episode. For example, a 30-45 second strip of EGM signals may include one or more PVC events that cause the AF detection algorithm of an IMD to designate a false R-wave marker. Based on the number of false R-wave markers in the EGM strip, the AF detection algorithm may determine that no arrhythmia episode is present or a false arrhythmia episode is present.

II. System Overview

FIG. 1 illustrates an implantable cardiac monitoring device (ICM) 100 intended for subcutaneous implantation at a site near the heart. The ICM 100 includes a pair of spaced-apart sense electrodes 114, 126 positioned with respect to a housing 102. The sense electrodes 114, 12 and 6 provide for detection of far field electrogram signals. Numerous configurations of electrode arrangements are possible. For example, the electrode 114 may be located on a distal end of the ICM 100, while the electrode 126 is located on a proximal side of the ICM 100. Additionally or alternatively, electrodes 126 may be located on opposite sides of the ICM 100, opposite ends or elsewhere. The distal electrode 114 may be formed as part of the housing 102, for example, by coating all but a portion of the housing with a nonconductive material such that the uncoated portion forms the electrode 114. In this case, the electrode 126 may be electrically isolated from the housing 114 electrode by placing it on a component separate from the housing 102, such as the header 120. Optionally, the header 120 may be formed as an integral portion of the housing 102. The header 120 includes an antenna 128 and the electrode 126. The antenna 128 is configured to wirelessly communicate with an external device 154 in accordance with one or more predetermined wireless protocols (e.g., Bluetooth, Bluetooth low energy, Wi-Fi, etc.). The housing 102 includes various other components such as: sense electronics for receiving signals from the electrodes, a microprocessor for processing the signals in accordance with algorithms, such as the AF detection algorithm described herein, a loop memory for temporary storage of CA data, a device memory for long-term storage of CA data upon certain triggering events, such as AF detection, sensors for detecting patient activity and a battery for powering components.

In at least some embodiments, the ICM 100 is configured to be placed subcutaneously utilizing a minimally invasive approach. Subcutaneous electrodes are provided on the housing 102 to simplify the implant procedure and eliminate a need for a transvenous lead system. The sensing electrodes may be located on opposite sides of the device and designed to provide robust episode detection through consistent contact at a sensor-tissue interface. The ICM 100 may be configured to be activated by the patient or automatically activated, in connection with recording subcutaneous ECG signals.

The ICM 100 senses far field, subcutaneous CA signals, processes the CA signals to detect arrhythmias and if an arrhythmia is detected, automatically records the CA signals in memory for subsequent transmission to an external device 154. The CA signal processing and AF detection is provided for, at least in part, by algorithms embodied in or implemented by the microprocessor. The ICM 100 includes one or more processors and memory that stores program instructions directing the processors to implement AF detection utilizing an on-board R-R interval irregularity (ORI) process that analyzes cardiac activity signals collected over one or more sensing channels.

Figure 2A:
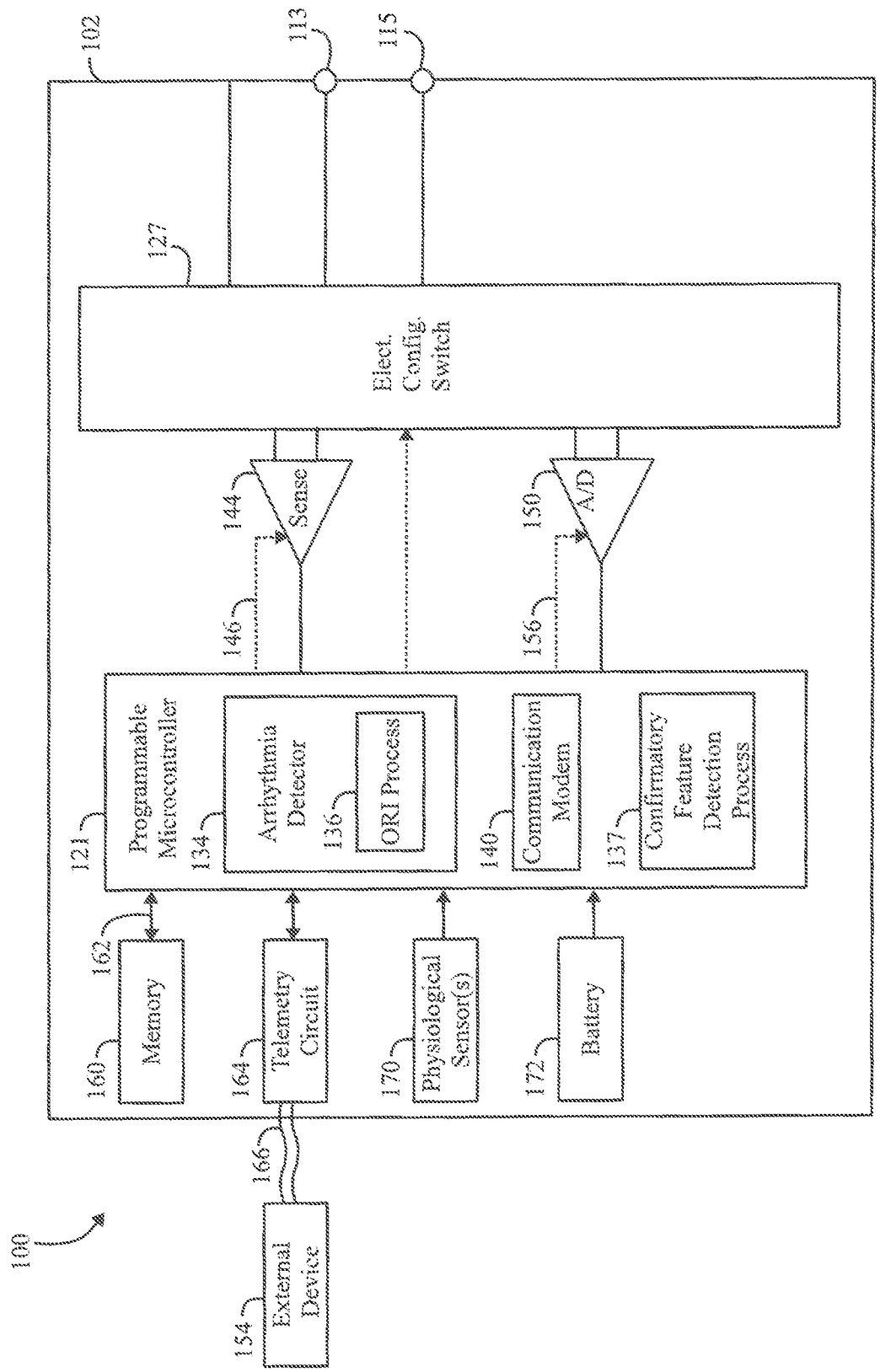
FIG. 2A shows a block diagram of the ICM formed in accordance with embodiments herein.

FIG. 2A shows a block diagram of the ICM 100 formed in accordance with embodiments herein. The ICM 100 may be implemented to monitor ventricular activity alone, or both ventricular and atrial activity through sensing circuitry. The ICM 100 has a housing 102 to hold the electronic/computing components. The housing 102 (which is often referred to as the "can", "case", "encasing", or "case electrode") may be programmably selected to act as an electrode for certain sensing modes. Housing 102 further includes a connector (not shown) with at least one terminal 113 and optionally additional terminals 115. The terminals 113, 115 may be coupled to sensing electrodes that are provided upon or immediately adjacent the housing 102. Optionally, more than two terminals 113, 115 may be provided in order to support more than two sensing electrodes, such as for a bipolar sensing scheme that uses the housing 102 as a reference electrode. Additionally or alternatively, the terminals 113, 115 may be connected to one or more leads having one or more electrodes provided thereon, where the electrodes are located in various locations about the heart. The type and location of each electrode may vary.

The ICM 100 includes a programmable microcontroller 121 that controls various operations of the ICM 100, including cardiac monitoring. Microcontroller 121 includes a microprocessor (or equivalent control circuitry), RAM and/or ROM memory, logic and timing circuitry, state machine circuitry, and I/O circuitry. The microcontroller 121 also performs the operations described herein in connection with collecting cardiac activity data and analyzing the cardiac activity data to identify AF episodes.

A switch 127 is optionally provided to avow selection of different electrode configurations under the control of the microcontroller 121. The electrode configuration switch 127 may include multiply switches for connecting the desired electrodes to the appropriate I/O circuits, thereby facilitating electrode programmability. The switch 127 is controlled by a control signal 128 from the microcontroller 121. Optionally, the switch 127 may be omitted and the I/O circuits directly connected to the housing electrode 114 and a second electrode 126. Microcontroller 121 includes an arrhythmia detector 134 that is configured to analyze cardiac activity signals to identify potential AF episodes as well as other arrhythmias (e.g., Tachycardias, Bradycardias, Asystole, etc.). By way of example, the arrhythmia detector 134 may implement an AF detection algorithm as described in U.S. Pat. No. 8,135,456, the complete subject matter of which is incorporated herein by reference. Although not shown, the microcontroller 121 may further include other dedicated circuitry and/or firmware/software components that assist in monitoring various conditions of the patient's heart and managing pacing therapies.

The ICM 100 is further equipped with a communication modem (modulator/demodulator) 140 to enable wireless communication. In one implementation, the communication modem 140 uses high frequency modulation, for example using RF, Bluetooth or Bluetooth Low Energy telemetry protocols. The signals are transmitted in a high frequency range and will travel through the body tissue in fluids without stimulating the heart or being felt by the patient. The communication modem 140 may be implemented in hardware as part of the microcontroller 121, or as software/firmware instructions programmed into and executed by the microcontroller 121. Alternatively, the modem 140 may reside separately from the microcontroller as a standalone component. The modem 140 facilitates data retrieval from a remote monitoring network. The modem 140 enables timely and accurate data transfer directly from the patient to an electronic device utilized by a physician.

The ICM 100 includes sensing circuitry 144 selectively coupled to one or more electrodes that perform sensing operations, through the switch 127 to detect cardiac activity data indicative of cardiac activity. The sensing circuitry 144 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the features of interest. In one embodiment, switch 127 may be used to determine the sensing polarity of the cardiac signal by selectively closing the appropriate switches.

The output of the sensing circuitry 144 is connected to the microcontroller 121 which, in turn, determines when to store the cardiac activity data of CA signals (digitized by the ND data acquisition system 150) in the memory 160. For example, the microcontroller 121 may only store the cardiac activity data (from the A/D data acquisition system 150) in the memory 160 when a potential AF episode is detected. The sensing circuitry 144 receives a control signal 146 from the microcontroller 121 for purposes of controlling the gain, threshold, polarization charge removal circuitry (not shown), and the timing of any blocking circuitry (not shown) coupled to the inputs of the sensing circuitry.

In the example of FIG. 2A, a single sensing circuit 144 is illustrated. Optionally, the ICM 100 may include multiple sensing circuits, similar to sensing circuit 144, where each sensing circuit is coupled to two or more electrodes and controlled by the microcontroller 121 to sense electrical activity detected at the corresponding two or more electrodes. The sensing circuit 144 may operate in a unipolar sensing configuration or hi a bipolar sensing configuration. Optionally, the sensing circuit 144 may be removed entirely and the microcontroller 121 perform the operations described herein based upon the CA signals from the A/D data acquisition system 150 directly coupled to the electrodes.

The arrhythmia detector 134 of the microcontroller 121 includes an on-board R-R interval irregularity (ORI) process 136 that detects AF episodes using an automatic detection algorithm that monitors for irregular ventricular rhythms that are commonly known to occur during AF. The ORI process 136 may be implemented as firmware, software and/or circuits. The ORI process 136 uses a hidden Markov Chains and Euclidian distance calculations of similarity to assess the transitionary behavior of one R-wave (RR) interval to another and compare the patient's RR interval transitions to the known RR interval transitions during AF and non-AF episodes obtained from the same patient and/or many patients. The ORI process 136 detects AF episodes over a short number of RR intervals. For example, the ORI process 136 may implement the AF detection methods described in U.S. Pat. No. 8,135,456, the complete subject matter of which is incorporated herein by reference in its entirety. As explained herein, the ORI process 136 manages a sensitivity profile of the sensor 144 during R-wave detection utilizing an automatic sensing control (ASC) adjustment to determine whether the CA signal has sufficient amplitude to be analyzed for cardiac events. The ORI process 136 identifies R-waves within the CA signals at points where the CA signal crosses the sensitivity profile (outside of a refractory period). The ORI process 136 tracks RR intervals within the CA signal and identifies AF events within the CA signal based on irregularities in the RR interval. When a sufficient number (e.g., X cardiac events out of Y cardiac events) of the cardiac events within the CA signal are identified as AF events, the ORI process 136 declares an AF episode.

Figure 3:
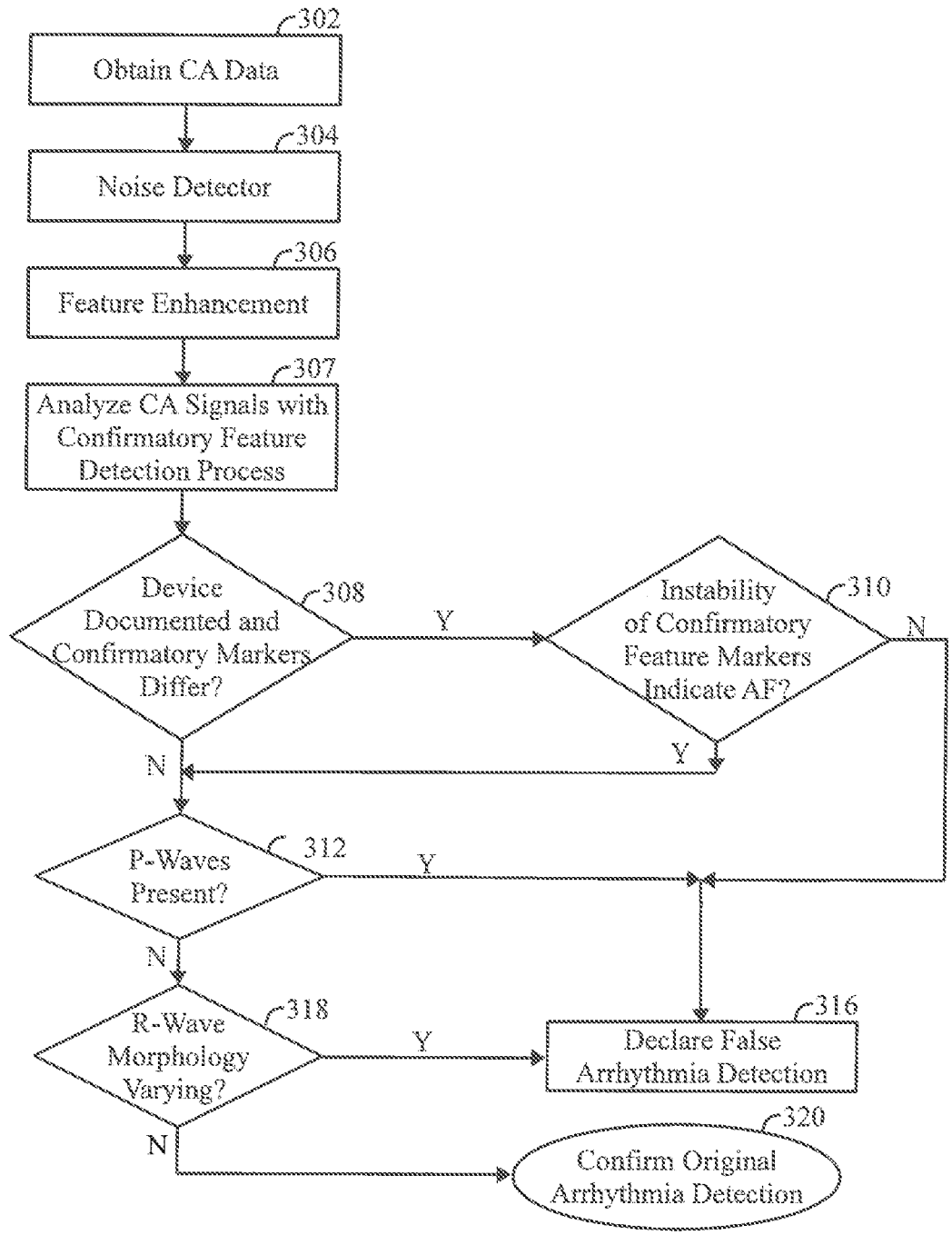
FIG. 3 shows a high-level workflow for an enhanced confirmatory AF detection process implemented in accordance with embodiments herein.
Figure 4:
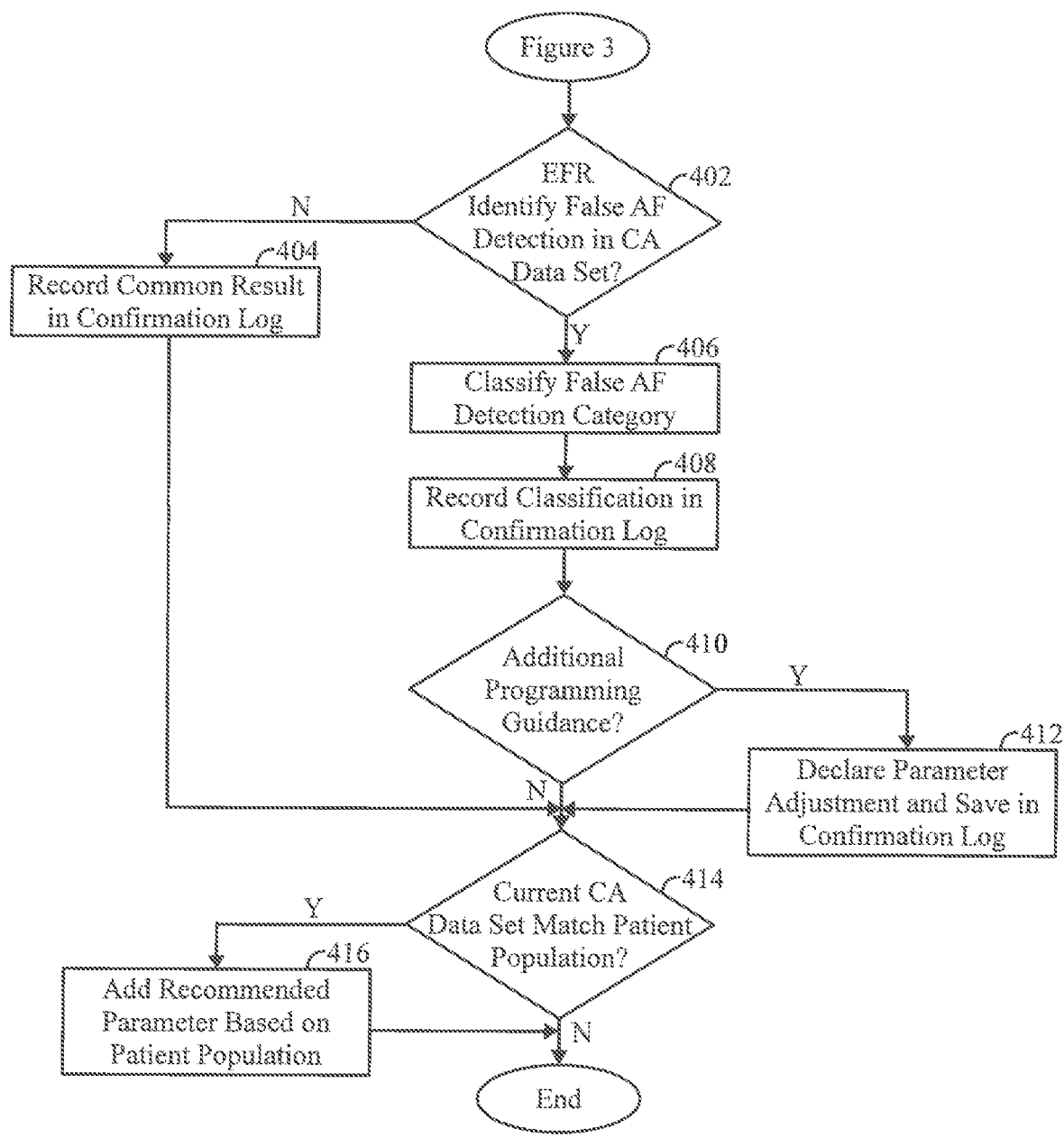
FIG. 4 illustrates a flow chart for classifying AF detection and developing recommendations for sensitivity profile parameter settings in accordance with embodiments herein.

Optionally, the microcontroller 121 may also include a confirmatory feature detection process 137 configured to implement one or more of the operations discussed herein, such as all or a portion of the enhanced confirmatory AF detection process of FIG. 3 and/or all or a portion of the AF detection classifying and recommendation process of FIG. 4. As a further example, the confirmatory feature detection process 137 may implement one or more of the R-wave detection processes, noise detection processes, P-wave detection processes and PVC detection processes described in the Co-Pending Related Applications.

Figure 2B:
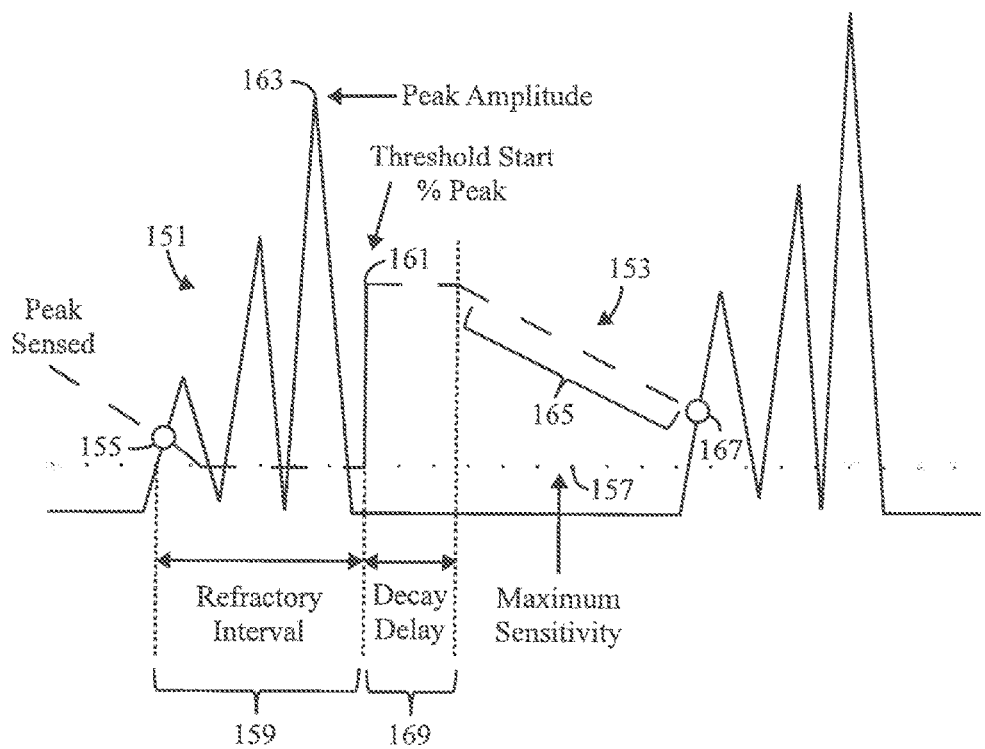
FIG. 2B illustrates an automatic sensing control adjustment utilized by the ORI process of the ICM in accordance with embodiments herein.

FIG. 2B illustrates an automatic sensing control adjustment utilized by the ORI process 136 of the ICM 100 in accordance with embodiments herein. FIG. 2B illustrates an example cardiac activity signal 151 after passing through a rectifier to convert all positive and negative deflections within the cardiac activity signal 151 to be positive deflections. The ORI process 136 manages the sensor 144 to have a sensitivity profile 153 (denoted by a dashed one) that varies over time.

In a basic implementation, the ORI process 136 utilizes a conventional automatic sensing control adjustment based on a conventional sensitivity profile 153. The sensitivity profile 153 is defined by sensitivity profile parameter settings corresponding to the threshold start sensitivity 161, decay delay time interval 169, maximum sensitivity 157 and slope of the sensitivity decay 165. Optionally, the sensitivity decay 165 may be defined in accordance with a non-linear monotonically changing shape from the threshold start sensitivity 161 to the maximum sensitivity 157. The start sensitivity parameter defines a start sensitivity of the sensitivity profile. For example, the start sensitivity parameter may set a start sensitivity to a percentage of the preceding R-wave peak amplitude. The refractory period/interval duration parameter defines a blanking interval beginning at a sensed R-wave, during which the processors do not search for a T-wave. The decay delay parameter defines the interval at which the sensitivity profile maintains the sensitivity level at a constant level following expiration of the refractory period before the sensitivity profile begins decreasing. When the sensitivity profile includes a linear sensitivity level decline, the decay delay rate defines a slope of the linear sensitivity level decline. The maximum sensitivity limit defines a lowest sensitivity level (e.g., maximum resolution) that linear sensitivity decline is allowed to reach. The sensitivity parameters are preprogrammed to fixed values and, over the operation of the IMD, are only modified (if at all) by a clinician.

In accordance with the sensitivity profile 153, when the CA signal 151 crosses the sensitivity profile 153 at starting point 155, the ORI process 136 treats the point 155 as a sensed R-wave and begins a refractory interval 159. No new R-wave (or T-wave) will be sensed during the refractory interval 159. At the end of the refractory interval 159, the sensitivity is adjusted to a threshold start sensitivity 161. The threshold start sensitivity 161 is defined as a percentage of the peak amplitude 163 of the QRS complex of the CA signal 151 detected during the refractory interval 159. The sensing circuit 144 maintains the threshold start sensitivity 161 for a decay delay time interval 169, after which the ORI process 136 begins to monotonically decrease the sensitivity (increase the resolution) of the sensing circuit 144 as denoted by the sensitivity decay 165 within the sensitivity profile 153. The sensing circuit 144 continues to decrease the sensitivity unto either the sensitivity decay 165 reaches the maximum sensitivity 157 or an amplitude of the rectified cardiac activity signal 161 exceeds the sensor sensitivity profile 153, such as at a point 167 where a new sensed R wave is detected.

The sensitivity of the sensing circuit 144 (FIG. 2A) is continuously adjusted by the microcontroller 121 in accordance with the sensitivity profile 153 over the course of an individual cardiac event. However, the conventional ORI process does not modify the parameter settings of the sensitivity profile beat by beat or on demand, sensitivity profile parameter In accordance with embodiments herein, the values of the sensitivity parameters may be adjusted based on whether the ORI process 136 is deemed to declare false AF detection R-waves. False AF detection may occur in connection with inappropriate R-wave sensing which may arise from under-sensing of R-waves and/or over-sensing of non-R-waves (e.g., noise, or P-waves, or T-waves as R-waves). For example, the confirmatory feature detection process 137 may determine when the ORI process 136 declares an undesirable number of false AF detections and in response thereto adjust one or more sensitivity profile parameters. Additionally or alternatively, the confirmatory feature detection process may be implemented external to the ICM 100, such as at a local external device or remote server. The local external device and/or remote server may then return, to the ICM 100, adjustments to the sensitivity profile parameters when an externally implemented confirmatory feature detection process identifies an undesirable number of false AF detections.

Returning to FIG. 2A, the ICM 100 further includes an analog-to-digital A/D data acquisition system (DAS) 150 coupled to one or more electrodes via the switch 127 to sample cardiac activity signals across any pair of desired electrodes. The data acquisition system 150 is configured to acquire cardiac electrogram (EGM) signals as CA signals, convert the raw analog data into digital data, and store the digital data as CA data for later processing and/or telemetric transmission to an external device 154 (e.g., a programmer, local transceiver, or a diagnostic system analyzer). The data acquisition system 150 is controlled by a control signal 156 from the microcontroller 121. The EGM signals may be utilized as the cardiac activity data that is analyzed for potential AF episodes. The ACS adjustment and ORI process 136 may be applied to signals from the sensor circuit 144 and/or the DAS 150.

By way of example, the external device 154 may represent a bedside monitor installed in a patient's home and utilized to communicate with the ICM 100 while the patient is at home, in bed or asleep. The external device 154 may be a programmer used in the clinic to interrogate the ICM 100, retrieve data and program detection criteria and other features. The external device 154 may be a handheld device (e.g., smartphone, tablet device, laptop computer, smartwatch and the like) that can be coupled over a network (e.g., the Internet) to a remote monitoring service, medical network and the like. The external device 154 facilitates access by physicians to patient data as well as permitting the physician to review real-time CA signals while collected by the ICM 100.

The microcontroller 121 is coupled to a memory 160 by a suitable data/address bus 162. The programmable operating parameters used by the microcontroller 121 are stored in memory 160 and used to customize the operation of the ICM 100 to suit the needs of a particular patient. Such operating parameters define, for example, detection rate thresholds, sensitivity, automatic features, AF detection criteria, activity sensing or other physiological sensors, and electrode polarity, etc.

In addition, the memory 160 stores the cardiac activity data, as well as the markers and other data content associated with detection of arrhythmia episodes. The operating parameters of the ICM 100 may be non-invasively programmed into the memory 160 through a telemetry circuit 164 in telemetric communication via communication link 166 with the external device 154. The telemetry circuit 164 allows intracardiac electrograms and status information relating to the operation of the ICM 100 (as contained in the microcontroller 121 or memory 160) to be sent to the external device 154 through the established communication link 166. In accordance with embodiments herein, the telemetry circuit 164 conveys the cardiac activity data, markers and other information related to AF episodes.

The ICM 100 may further include magnet detection circuitry (not shown), coupled to the microcontroller 121, to detect when a magnet is placed over the unit. A magnet may be used by a clinician to perform various test functions of the housing 102 and/or to signal the microcontroller 121 that the external device 154 is in place to receive or transmit data to the microcontroller 121 through the telemetry circuits 164.

The ICM 100 can further include one or more physiologic sensors 170. Such sensors are commonly referred to (in the pacemaker arts) as "rate-responsive" or "exercise" sensors. The physiological sensor 170 may further be used to detect changes in the physiological condition of the heart, or diurnal changes in activity (e.g., detecting sleep and wake states). Signals generated by the physiological sensors 170 are passed to the microcontroller 121 for analysis and optional storage in the memory 160 in connection with the cardiac activity data, markers, episode information and the like. While shown as being included within the housing 102, the physiologic sensor(s) 170 may be external to the housing 102, yet still be implanted within or carried by the patient. Examples of physiologic sensors might include sensors that, for example, activity, temperature, sense respiration rate, pH of blood, ventricular gradient, activity, position/posture, minute ventilation (MV), and so forth.

A battery 172 provides operating power to all of the components in the ICM 100. The battery 172 is capable of operating at low current drains for long periods of time. The battery 172 also desirably has a predictable discharge characteristic so that elective replacement time can be detected. As one example, the housing 102 employs lithium/silver vanadium oxide batteries. The battery 172 may afford various periods of longevity (e.g., three years or more of device monitoring). In alternate embodiments, the battery 172 could be rechargeable. See for example, U.S. Pat. No. 7,294,108, Cardiac event micro-recorder and method for implanting same, which is hereby incorporated by reference.

The ICM 100 provides a simple to configure data storage option to enable physicians to prioritize data based on individual patient conditions, to capture significant events and reduce risk that unexpected events are missed. The ICM 100 may be programmable for pre- and post-trigger event storage. For example, the ICM 100 may be automatically activated to store 10-120 seconds of CA data prior to an event of interest and/or to store 10-120 seconds of post CA data. Optionally, the ICM 100 may afford patient triggered activation in which pre-event CA data is stored, as well as post event CA data (e.g., pre-event storage of 1-15 minutes and post-event storage of 1-15 minutes). Optionally, the ICM 100 may afford manual (patient triggered) or automatic activation for CA data. Optionally, the ICM 100 may afford additional programming options (e.g., asystole duration, bradycardia rate, tachycardia rate, tachycardia cycle count). The amount of CA data storage may vary based upon the size of the memory 160.

The ICM 100 may provide comprehensive safe diagnostic data reports including a summary of heart rate, in order to assist physicians in diagnosis and treatment of patient conditions. By way of example, reports may include episodal diagnostics for auto trigger events, episode duration, episode count, episode date/time stamp and heart rate histograms. The ICM 100 may be configured to be relatively small (e.g., between 2-10 cc in volume) which may, among other things, reduce risk of infection during implant procedure, afford the use of a small incision, afford the use of a smaller subcutaneous pocket and the like. The small footprint may also reduce implant time and introduce less change in body image for patients.

Figure 2C:
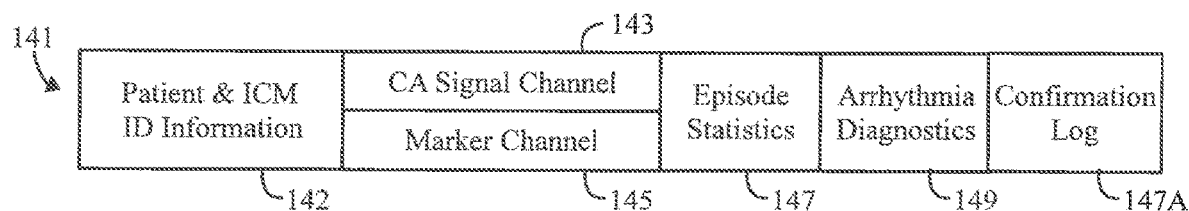
FIG. 2C illustrates cardiac activity data generated and stored by an ICM in accordance with embodiments herein.

FIG. 2C illustrates cardiac activity data generated and stored by the ICM 100 in memory 160 in accordance with embodiments herein. The CA data 141 is stored by the ICM in response to detection of episodes of interest, patient initiated instructions, physician initiated instructions and the like. The CA data 141 may include, among other things, patient and ICM identification information 142. By way of example, the patient identification information may include a patient unique medical record number or other identifier, patient name and/or patient demographic information. The ICM ID may include a serial number or other unique identifier of the ICM, software and firmware version numbers, and/or a unique wireless ID. The CA data 141 includes one or more signal channels 143 that store CA signals collected by a corresponding sensing channel (e.g., sensor circuit 144 or DAS 150). The CA signal channel 143 may include EGM signals for a series of cardiac beats/events sensed by the ICM. The CA data 141 also includes a marker channel 145 having, among other things, device documented markers identified by the ICM 100 in connection with the CA signal. The device documented markers within the marker channel 145 may include device documented markers indicative of normal sinus features, AF detected events, AF detected episodes and the like. For example, the ORI process 136 (FIG. 2A) utilizes the sensitivity profile 153 (FIG. 2B) to identify R-waves in the CA signal.

The content of the CA signal channel 143 and marker channel 145 may be displayed on a display of an external device (e.g., smart phone, tablet device, computer, smart watch, etc.) as corresponding types of CA and marker waveforms (e.g., in a rhythm display screen). In the present example, a single CA signal channel 143 is described in connection with a single CA signal. Optionally, embodiments herein may be implemented in connection with multiple CA signal channels. For example, the ICM 100 may be configured to include multiple sensing channels with different sensing characteristics. As one example, a first sensing channel may be configured to perform full range signal sensing, such as in connection with detecting R-waves (corresponding to the CA signal channel 143). A second sensing channel may be configured to perform narrow range signal sensing, such as in connection with detecting P-waves which have much smaller amplitude in comparison to the R-waves. Optionally, multiple ECG signals may be displayed in parallel and temporally aligned with EGM and marker waveforms.

The CA data 141 also includes episode statistics 147 and arrhythmia diagnostics 149. The episode statistics 147 may be presented in a window on a user interface to list various statistical data for any or all episodes recorded by the ICM 100 since the episode and CA data storage were last cleared. Optionally, the episode statistics 147 may also list the number of inhibited VT diagnoses due to arrhythmia qualifiers, such as a bigeminal rhythm qualifier, and/or other rhythm discriminators. As further non-limiting examples, the episode statistics 147 may also include a date of a last programmer session, date of the last ICM interrogation, the date of the presently stored episodes and the date when EGMs were last cleared from the ICM and the like.

Figure 2D:
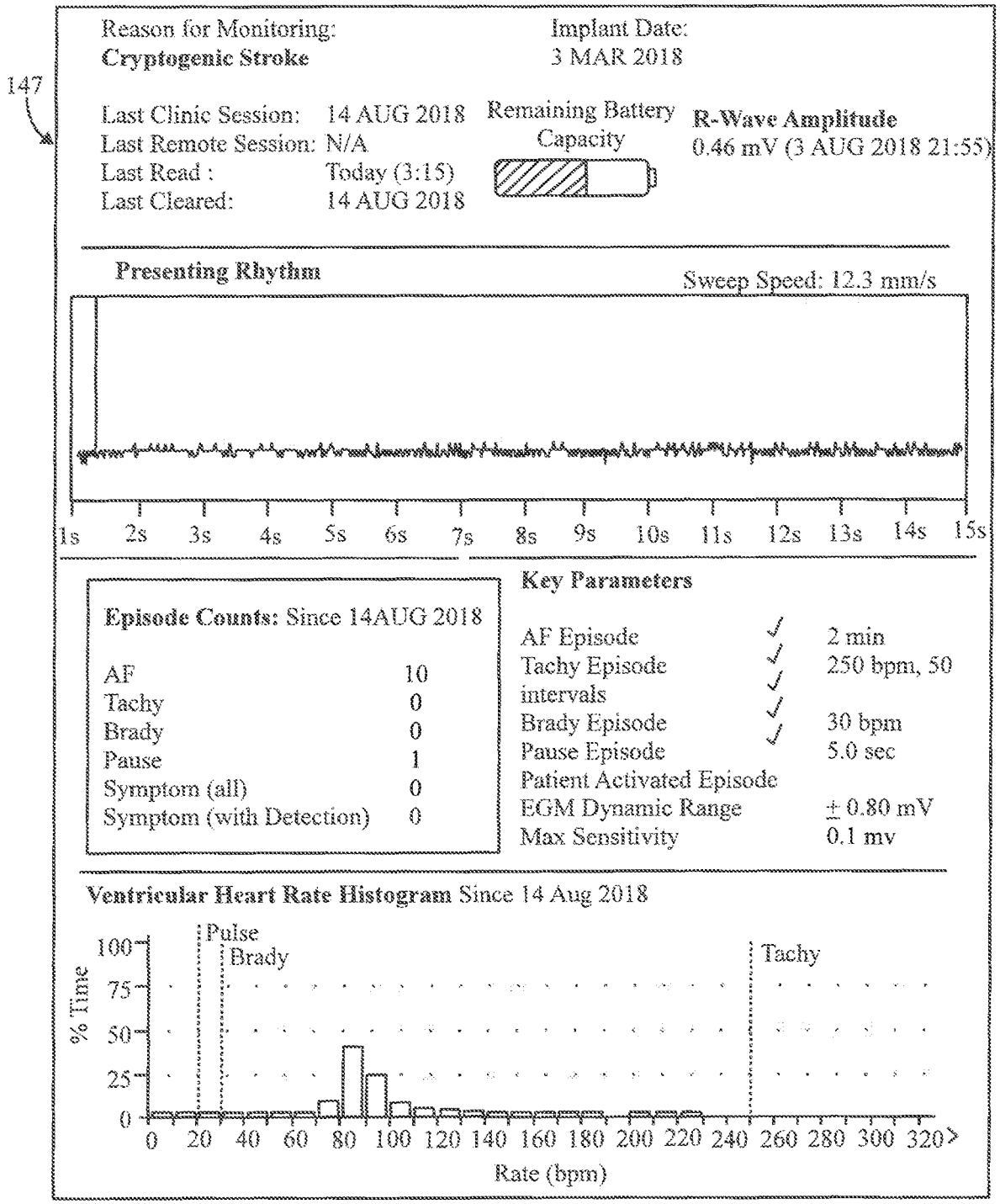
FIG. 2D illustrates screenshots of displays in which episode statistics and arrhythmia diagnostics may be presented to a physician in accordance with an embodiment herein.
Figure 2E:
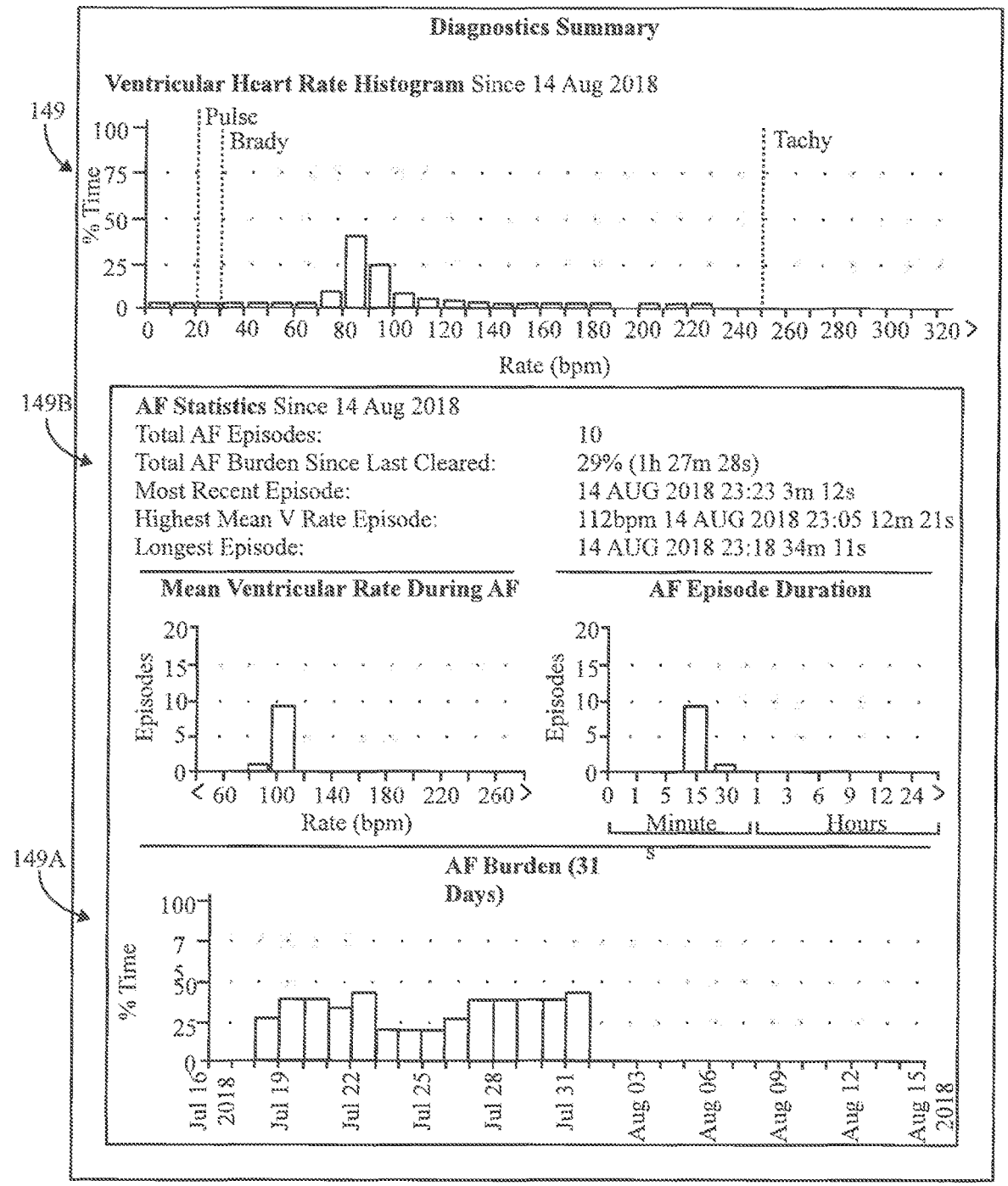
FIG. 2E illustrates screenshots of displays in which episode statistics and arrhythmia diagnostics may be presented to a physician in accordance with an embodiment herein.

FIGS. 2D and 2E illustrate screenshots of displays in which episode statistics and arrhythmia diagnostics may be presented to a physician in accordance with an embodiment herein. The arrhythmia diagnostics 149 may represent cumulative diagnostic information for a period of time, such as when the diagnostics data is last cleared from the ICM. The arrhythmia diagnostics 149 may include various information concerning heart rate, such as ventricular heart rate histograms, dates and times of last programmer sessions, diagnostic data last read, diagnostic data last cleared and the like. The arrhythmia diagnostics 149 may also include AF diagnostics, such as AF burden 149A, AF summaries, AF statistical data 149B, dates and times of last programmer session, last time the AF diagnostic data were read, last time the AF diagnostic data was cleared and the like. By way of example, AF burden may be displayed in an AF diagnostics window of a computing device formatted as one or more bar graphs of a percentage of time (as shown in FIG. 2E) that the patient experienced AF during a predetermined period of time (e.g., each day, each week, each month). The AF burden may show a percentage of time that the patient was in AF since the AF diagnostics data were last cleared. The AF summary may include one or more graphs of mean ventricular heart rate and a duration of AF episodes since the AF diagnostic data were last cleared. The AF diagnostic data may accrue various cumulative totals concerning AF episodes detected and/or stored since the AF diagnostic data were last cleared. The AF statistics may include, among other things, a total number of AF episodes, AF burden trends, AF episode duration histograms, mean ventricular rate during AF and the like.

As explained herein, an enhanced confirmatory AF detection process is implemented to analyze the results of the baseline analysis performed by the ORI process in the ICM. The enhanced confirmatory AF detection process determines whether AF episodes declared by the ICM are true or false, and updates the AF diagnostics in connection there with. Next, various processes are described in connection with embodiments herein that are performed by one or more of the circuits, processors and other structures illustrated in the figures and described in the specification.

FIG. 3 shows a high-level workflow for an enhanced confirmatory AF detection process implemented in accordance with embodiments herein. By way of example, the operations of FIG. 3 may be implemented, as a confirmatory process, where cardiac activity signals have been previously analyzed by an AF detection module, such as the ORI process described in connection with FIGS. 2A and 2B. The process may initiate the operations of FIG. 3 in an attempt to verify whether one or more episodes in a CA data set, are in fact an AF episode or a normal rhythmic/sinus episode. Optionally, the operations of FIG. 3 may be implemented in connection with a CA data set that has not been previously analyzed for potential AF episodes. The operations of FIG. 3 may be implemented as part of a local or distributed system, such as by the microcontroller 121 of the ICM, by a local external device and/or a remote server.

At 302, one or more processors of the system obtain a cardiac activity (CA) data set including CA signals recorded in connection with a series of cardiac events. The CA data includes device documented arrhythmic markers including identifying AF entry and/or exit within the series of cardiac events. The CA data also includes device documented rhythmic markers (e.g., R-wave) to identify the cardiac beats sensed by the device within the series of cardiac events. The CA data also include device documented activity and noise markers to identify periods of time under significant physical activity and/or noise interrupt within the series of cardiac events. All device documented markers are declared and designated by the ICM utilizing the ORI process to analyze the CA signals.

For example, the cardiac activity data may be obtained by an external monitoring device or ICM that includes electrodes that sense CA signals, such as electrocardiogram (ECG) signals and/or intra-electrocardiogram (EGM) signals. The ECG and/or EGM signals may be collected by a subcutaneous ICM that does not include a transvenous lead or otherwise experiences difficulty in sensing P-waves and/or R-waves. The cardiac activity data may have been previously acquired and stored in memory of an implantable or external monitoring device, implantable or external therapy delivery device, programmer, workstation, healthcare network or other system. When the cardiac activity data has been previously acquired, the obtaining operation at 302 represents accessing and reading the previously stored cardiac activity data.

The operations of FIG. 3 may be staged to be performed upon the CA data at various times, such as in real time (e.g., during or shortly after a patient experiences an episode) or at any time after storage of the CA data. The operations of FIG. 3 may be performed by devices and systems at various proximity to a patient with the ICM. For example, the CA data may be read out of an ICM and transmitted to a local portable external device (e.g., smartphone, table computer, laptop computer, smartwatch, etc.), where the local portable external device locally implements all or a portion of the operations described in connection with FIG. 3 while in close proximity to the patient. Additionally or alternatively, the CA data may be read out of the ICM to a local portable external device and transmitted to a remote server, medical network, physician computer and the like, which implements all or a portion of the operations described in connection with FIG. 3 remote from the patient. Additionally or alternatively, the CA data may be read from the ICM by a programmer device, such as during a patient visit to a physician, where the programmer device implements all or a portion of the operations described in connection with FIG. 3 during or after a patient-doctor visit.

The CA data may include CA signals for a series of cardiac events spanning over various periods of time. As one example, one segment or set of the cardiac activity data may be collected for an interval that is 30 seconds to 5 minutes in length and that includes one or more ICM declared AF episodes. As another example, one segment or set of the cardiac activity data may be collected for an interval that begins 10-60 seconds before an episode of interest (e.g., an AF episode) and that ends 10-60 seconds after the episode of interest. A CA data set may include one or multiple AF episodes. The duration of a CA data set may be programmed for a predetermined period of time based on detection of AF episodes and/or based on other criteria. The predetermined period of time may be programmed by a clinician, or automatically updated by one or more processors throughout operation. By way of example, the predetermined period of time may correspond to one minute, 30 minutes, one hour or otherwise. The CA data obtained at 302 may correspond to one detected AF episode and/or multiple detected AF episodes. The CA data set obtained at 302 may correspond to one continuous series of cardiac events (e.g., 1 continuous series for 30 seconds to 5 minutes) and/or separate sets of cardiac events (3-10 separate series, each for 30 seconds to 3 minutes of cardiac events).

Collection and analysis of CA signals by the ICM may be initiated automatically when the ICM detects an episode of interest. Additionally or alternatively, the ICM may collect and analyze CA signals in response to a user-initiated instruction. For example, a user may utilize a smart phone or other portable device to establish a communications session with the ICM and instruct the ICM to begin to collect and analyze cardiac signals, such as when the patient is experiencing discomfort, feeling faint, a rapid heart rate, etc.

At 304 to 320, the one or more processors determine whether the onboard RR interval irregularity process (implemented by the ICM_declared one or more false positive AF episodes, such as due to under-sensing or over-sensing features within the CA signal. The operations at 304 to 320 generally perform an R-wave enhancement and feature rejection (EFR) process. The EFR process enlarges or exaggerates features of interest (e.g., R-wave) within the CA signal and optionally suppresses at least certain features not of interest (e.g., non-R-wave features such as noise, T-waves) to obtain confirmatory feature markers. The EFR process applies a series of tests to confirm or reject alternative conditions that a patient may have experienced. The operations at 306 to 320 confirm or reject a presence or absence of certain rhythmic, physiologic and non-physiologic (e.g., noise) features within the CA data. Non-limiting examples of the features, for which the process searches include noise, R-wave changes, P-waves, and post ventricular contractions.

At 304, the one or more processors analyze the CA data for noise and pass or remove segments of the CA signal for select cardiac events based on a noise level within the corresponding segment of the CA signal. The noise is identified based on noise discrimination parameters that are set to a desired sensitivity level. While the sensitivity of the noise detection process at 304 may be adjusted, the sensitivity of the noise detection process at 304 is more selective than the on-board noise detection circuit in the ICM. For example, at 304, the one or more processors may implement the noise detection process described in one or more of the Co-Pending Related Applications referred to above, filed concurrently on the same day as the present application. For example, the operation at 304 generally represents a software based evaluation of the CA data to detect noise. The software based evaluation can be developed in a manner that is tailored to AF detection such that the software-based noise rejection is more sensitive in connection with identifying or removing unduly noisy CA signal segments that in turn give rise to inappropriate R-wave detection, leading to false AF episodes declaration by the ICM. The original CA data processed in connection with FIG. 3 results from the onboard ORI process of the ICM. The onboard ORI process processes incoming signals that have first passed through a hardware-based noise detect that applies noise discrimination the hardware-based noise detector is not as sensitive as, and not as adaptable as, the software based noise discrimination implemented at 304. Also, depending upon a complexity of the software-based noise discrimination, processors of an ICM may not have a sufficient processing power to implement the software noise discrimination. The extent to which the software-based noise discrimination may be implemented on an ICM depends in part upon the sensitivity level desired. For example, the discrimination parameters may be set to a very "conservative" level such that the noise detector only eliminates CA signals for cardiac events that include a substantial amount of noise (e.g., the signal to noise ratio is less than or equal to 50%). Levels for the noise discrimination parameters may be adjusted to eliminate more cardiac events that include relatively intermediate levels of noise (e.g., the signal to noise ratio is between 75% and 90%). The noise discriminator passes CA signals for cardiac events that have less noise than the level defined by the noise discrimination parameters.

Optionally, at 304, when the noise level is sufficiently high (e.g., satisfying a threshold), the initial AF diagnosis/declaration by the ICM may be overridden. For example, when the noise level exceeds a threshold in connection with an AF episode declared by the ICM, the processors may cancel the AF episode declaration and reset any counters set in connection there with.

At 306, the one or more processors apply a feature enhancement process to form modified CA signals in which sinus features of interest are enlarged or exaggerated relative to the original/baseline CA signals. Optionally, at least certain features not of interest (e.g., noise, T-waves) are reduced or suppressed relative to the baseline CA signals in order to generate the confirmatory feature (e.g., R-wave) marker. For example, at 306, the one or more processors may implement the feature enhancement process described in one or more of the Co-Pending Related Applications referred to above, filed concurrently on the same day as the present application.

At 307, the one or more processors analyze the modified CA signal utilizing a confirmatory feature detection process. For example, at 306, the one or more processors may implement, as the confirmatory feature detection process, the R-wave detection processes described in one or more of the Co-Pending Related Applications referred to above, and filed concurrently on the same day as the present application. The processors analyze the modified CA signal to identify R-waves, and store a set of confirmatory feature markers separate and distinct from the device documented (DD) feature markers.

At 308, the one or more processors determine whether the confirmatory feature markers match or differ from the DD feature markers. For example, the determination at 308 may be based on a simple count of the number of DD feature markers as compared to a count of the number of confirmatory feature markers. Additionally or alternatively, the determination at 308 may determine whether the confirmatory feature detection process identified confirmatory feature markers (e.g., R-waves) from the CA signals that were not identified by the ORI process or displaced significantly. For example, the DD and confirmatory feature markers for the CA data may be aligned temporally and compared to identify differences.

Differences may occur due to various reasons. For example, the ORI process may under-sense R-waves, while the confirmatory feature detection process properly identifies a feature of interest in the modified CA signal as an R-wave. As another example, the ORI process may over sense R-waves, while the confirmatory feature detection process properly determines that no R-wave is present in a particular segment of the CA signal. Additionally or alternatively, a difference may be declared when the ORI process and confirmatory feature detection process both declare an R-wave for a specific cardiac event, but the DD and confirmatory R-waves are temporally offset from one another in time by more than a desired R-wave offset threshold.

When the process determines at 308 that a difference or change exists between the confirmatory and DD feature markers, flow moves to 310. When the process determines that no difference or change exists between the confirmatory and DD feature markers, flow moves to 312. At 310 the one or more processors identify instability in the confirmatory feature markers. At 310, the one or more processors determine whether the instability within the confirmatory feature marker indicates AF. The processors determine the presence or absence of instability by analyzing variation in the RR intervals between the confirmatory features markers, such as using the processors described in the Co-Pending Related Application and/or the '456 patent. If the instability/variation equals or is below a stability threshold, the segment of the CA signal is considered to exhibit a stable feature-to-feature interval that does not indicate AF. Consequently, flow moves to 316. Alternatively, when the instability is above the instability threshold, the analysis of the CA signal segment is considered to exhibit an unstable feature-to-feature interval. Consequently, flow moves to 312.

At 316, when AF is not indicated, the one or more processors classify an episode in the CA data set to be a DD false positive or false detection. At 316, the one or more processors may perform additional operations, such as setting one or more flags to track the declaration of DD false positives by the ORI process on the ICM. Additionally or alternatively, at 316, the one or more processors may reverse a diagnosis of AF, adjust various statistics tracking the patient's behavior and the like. For example, the AF diagnostics (e.g., 149 in FIG. 2C) may be updated to correct for false AF detection. Additionally or alternatively, a memory segment within the ICM that includes the CA data set associated with a false AF detection may be set to have a lower priority. Reassignment of priority levels to different memory segments may be utilized in connection with overwriting memory segments during future use. For example, when the CA data memory of the ICM approaches or becomes full, the memory segment assigned the lowest priority may then be overwritten first when the ICM detects new AF episodes.

When flow advances to 312, the potential still exists that the CA signals does not include an AF episode. Therefore, the process of FIG. 3 performs additional analysis upon the CA data. At 312, the one or more processors perform a P-wave detection operation to determine whether P-waves are present within the CA signal segment being analyzed. For example, at 312, the one or more processors may implement the P-wave detection process described in one or more of the Co-Pending Related Applications referred to above, and filed concurrently on the same day as the present application. When a P-wave is identified to be present in the CA signal, the process determines that the presence of a P-wave indicates that the current episode is not an AF episode even though RR interval irregularity may be present. Accordingly, flow moves to 316.

Alternatively, at 312 when the one or more processors determine that no P-waves are present within the CA signal, a potential still remains that the CA signal does not correspond to an AF episode. Accordingly, flow advances to 318 where additional analysis is applied to the CA data set. At 318, the one or more processors apply a morphology based premature ventricular contraction (PVC) detection operation. For example, at 318, the one or more processors may implement the QRS complex morphology based PVC detection process described in one or more of the Co-Pending Related Applications referred to above, and filed concurrently on the same day as the present application. The processors determine whether a QRS complex morphology has varied beyond a morphology variation threshold. Variation in the R-wave morphology beyond the morphology variation threshold provides a good indicator that the cardiac events include one or more PVC. When the cardiac events include a sufficient number of PVCs, the process may attribute an R-R interval variation to (and indicative of) PVCs or non-atrial originated beats that lead to significantly different R-R intervals, and not due to (or indicative of) an AF episode. Accordingly, when the R-wave morphology exceeds the morphology variation threshold, flow returns to 316, where the process performs the operations described herein. At 316, one or more flags may be set to indicate that the false AF detection was declared due to one or more PVCs present within the CA data. Additionally or alternatively, a diagnosis may be changed from AF episode to PVC episode. The number of PVC may vary that are needed to achieve an R-wave morphology variation at 318 sufficient for flow to branch to 316 (e.g., declare a false AF detection).

At 318, alternatively, when the R-wave morphology does not exceed the morphology variation threshold, the process interprets the condition as an indicator that the cardiac events do not include significant number of PVCs. Thus, flow moves to 320. At 320, the one or more processors confirm a device documented AF episode and records the current episode to remain as originally declared by the ORI process.

Optionally, the sequence of operations discussed in connection with FIG. 3 may be changed and/or some of the operations may be omitted depending on computational and performance objectives. For example, it may be determined that a low probability exists that a particular patient (or ICM) experiences PVCs that cause false AF detection, and thus, the process of FIG. 3 may omit the PVC detection operation at 318. Additionally or alternatively, it may be determined that a low probability exists that an ICM is incorrectly detecting P-waves as R-waves that would cause false AF detection, and thus, the process of FIG. 3 may omit the P-wave detection operation at 312.

Additionally or alternatively, it may be determined that less processing time/power is utilized to identify P-waves (operations at 312) and/or PVCs (operations at 318) that cause false AF detection, as compared to R-wave detection and analysis of RR interval stability (operations at 306-310). Accordingly, the P-wave and/or PVC detection operations may be performed before the R-wave detection and analysis. In the present example, in the event a P-wave or PVC is detected, the process may declare a CA data set to include a false AF detection without performing the further computations for R-wave detection and analysis.

Optionally, the operations at 308-318 may be modified to not represent binary branches between alternative paths. Instead, the decisions at operations 308-318 may result in a score or a vote, rather then a binary "AF" or "not AF". The vote or score may be variable based upon a degree to which the feature of interest in the confirmatory analysis matches the determination from the original ORI process. Additionally or alternatively, the vote or score may be based on a degree to which the feature of interest from the confirmatory analysis matches one or more baseline values. The votes or scores may be used in conjunction with other AF detection algorithms in order to find a probability that an AF episode has occurred.

The operations of FIG. 3 may be repeated periodically or in response to detection of particular criteria, such as detection of potential atrial fibrillation episodes or otherwise.

The operations of FIG. 3 afford a powerful, sophisticated process to confirm AF detection within ECG and EGM signals in a non-real time manner. The AF detection confirmation processes described herein may utilize computationally expensive analysis that may otherwise not be to be implemented in an on-board circuit within an ICM, either due to memory and power constraints, processing power constraints, and/or an inability to complete the analysis in real time.

Optionally, the operations of one or more of the stages within the process of FIG. 3 may be adapted to run in ICM firmware, although firmware Implementations may exhibit different overall performance. In a firmware implementation, a similar form of step-by-step discrimination on existing AF episodes may be achieved. Alternatively, some or all of the features may be adapted for real-time use and set as additional or alternative signals. For example, the determinations at 306-318 may produce factors that are applied to an AF probability and sudden onset determination as AF detection criteria.

FIG. 4 illustrates a flow chart for classifying AF detection and developing recommendations for sensitivity profile parameter settings in accordance with embodiments herein. For example, the operations of FIG. 4 may be performed at 316 and/or 320 in FIG. 3 and/or at other points in the processes described herein. The operations of FIG. 4 build and/or add to a confirmation log that tracks and records the differences and similarities between the results of the EFR and ORI processes. The confirmation log may be stored together with, or separate from, the underlying baseline CA data set and/or the modified CA data set. Optionally, the confirmation log may not represent a separate file, but instead merely represent parameter settings or other information appended to the original or modified CA data set. For example, the confirmation log may be saved as metadata or otherwise appended to the CA data set.

At 402, the one or more processors of the system determine whether the EFR process identified one or more false AF detection by the ORI process applied by the ICM. When the EFR process and the ORI process detect a common or similar number/degree of AF episodes in the CA data set, flow moves to 404. At 404, the one or more processors record a match between the results of the EFR and ORI processes. The match is stored in the confirmation log. When the EFR process identifies a false AF detection that was declared by the ORI process, flow moves to 406.

At 406, the one OF more processors classify the false AF detection into one of multiple different categories. Non-limiting examples of the categories include noise, inappropriate sensing, irregular sinus rhythm, frequent PVCs and the like. The processors may classify the false AF detection as noise when the baseline CA data set is determine to have an excessive amount of noise (at 302). For example, the excessive amount of noise may be determined when a number of cardiac events that are removed/suppressed (at 304, 312, 318) exceeds a threshold and/or exceeds a percentage of the total number of cardiac events in the CA data set. The processors may classify the false AF detection as inappropriate sensing when the feature detection (at 306) determines that the CA data includes more or few features of interest (e.g., under-sensed R-waves or over-sensed false R-waves). The processors may classify the false AF detection as sinus rhythm when the P-wave detection (at 312) determines that the CA data set includes one or more P-waves. The processors may classify the false AF detection as frequent PVCs when the PVC detection (at 318) determines that the CA data exceeds a PVC threshold.

At 408, the one or more processors record the classification identified at 406 in the confirmation log. At 410, the one or more processors determine whether additional guidance is to be provided for setting sensitivity profile parameters of the ICM. For example, the processors, at 410, may determine whether an extent or degree of the false R-wave and AF detection (e.g., number of under-sensed R-waves, number of P-waves (as well as T-wave or noise artifact) classified as R-waves, number of frequent PVCs) exceeds a threshold that justifies adjusting one or more sensitivity profile parameters of the ICM. When sensitivity profile parameter adjustments can be made, flow moves to 412. Otherwise, flow continues to 414.

When the extent or degree of the false R-wave and AF detection warrants a parameter adjustment, the sensitivity profile parameter adjustment is determined based in part on the classification at 406. At 412, the one or more processors declare an adjustment to the sensing parameters based on a nature and/or extent of the false R-wave and AF detection. For example, when a false AF detection is classified as due to inappropriate sensing, the processors may declare the sensitivity profile parameter adjustment to be an increase or decrease in the feature (e.g., R-wave) detection threshold. As another example, the processors may declare the sensitivity profile parameter adjustment to be an increase in the R-wave detection threshold when P-waves are identified as R-waves by the ORI process. As another example, the processors may declare the sensitivity profile parameter adjustment to be an increase in the decay delay value when the ORI process over senses T-waves and designates the T-waves to be R-waves. The sensitivity profile parameter adjustment is saved in the confirmation log. Optionally, the confirmation log may also maintain a PVC count.

The increase or decrease in the sensitivity profile parameter adjustment may be a predefined step (e.g., increase threshold by X mV or Y %). Optionally, the increase or decrease may be based on an extent or nature of the false R-wave and AF detection. For example, when the ORI process under-sensed multiple R-waves in the CA data set, the process may decrease the R-wave detection threshold by a larger factor as compared to when the ORI process under-senses one or a few R-waves out of multiple R-waves. As another example, a decay delay value adjustment and/or refractory period value adjustment may be determined based in part on a number of T waves sensed as R-waves, a timing between the T waves and corresponding preceding R-waves, and/or a peak amplitude of the T waves relative to the sensing sensitivity at the time the T-wave is detected.

Optionally, the one or more processors may identify additional or alternative sensitivity profile parameter adjustments based on a database of sensitivity profile parameter settings that are correlated to cardiac activity data for a patient population. For example, a database may be maintained of EGM or ECG data segments collected in connection with numerous patients that experienced AF, sinus rhythms and/or other arrhythmias, where the EGM/ECG data segments are correlated with sensitivity profile parameter settings that are used by a monitoring device to collect the EGM or ECG data. The patient population database may also indicate which sensitivity profile parameter settings achieved desired results and which sensitivity profile parameter settings did not achieve desired results. The database may further include quality indicators indicative of whether the sensitivity profile parameter settings were deemed to collect good or accurate results (e.g., correctly sense R-waves without over-sensing P-waves or T waves, and correctly sense all R-waves without under-sensing of R-waves with smaller amplitude). The database may further include quality indicators indicative of whether the sensitivity profile parameter settings were deemed to accurately declare AF detection in a high percentage of the instances of AF. The quality indicators may be automatically entered based on automated analysis of the data within the database and/or entered by physicians or other medical personnel as sensitivity profile parameter settings are adjusted for individual patients. The database may be available on a medical network, through a cloud computing service and/or other local or remote source.

At 414, the one or more processors compare the current false AF detection, modified CA data set and/or baseline CA data to a database of third-party CA data sets and false/valid AF detections for other patients. The processors may identify matches or similarities between the false/valid AF detection, modified CA data set and/or baseline CA data set, for the current patient, and the corresponding type of AF detections and third-party CA data set from the database of the larger population. When no match occurs, the operations of FIG. 4 end. Alternatively, when one or more matches occur between the current CA data set and the patient population database, flow moves to 416. At 416, the one or more processors identify additional or alternative sensitivity profile parameter adjustments to record in the confirmation log for the present patient based on the matches or similar cases from the database and the present patient.

The sensitivity profile parameter adjustments, in the confirmation log, may be presented on a display of a mobile device, computer, workstation, etc., as a suggestion or option ICM for the physician or other medical personnel to apply to a current. Optionally, the sensitivity profile parameter adjustments may be pushed and uploaded to the ICM from a local portable external device and/or a remote medical network. The sensitivity profile parameter adjustments may be pushed to the ICM at the direction of the physician or other medical personnel, after the physician or medical personnel has reviewed the baseline and/or modified CA data (with R-wave and AF markers) and other statistical information concerning one or more episodes experienced by the patient. Additional or alternatively, the sensitivity profile parameter adjustments may be automatically pushed and uploaded to the ICM at the conclusion of the operations of FIG. 4, such as when the adjustment is within a predetermined limit.

Figure 5:
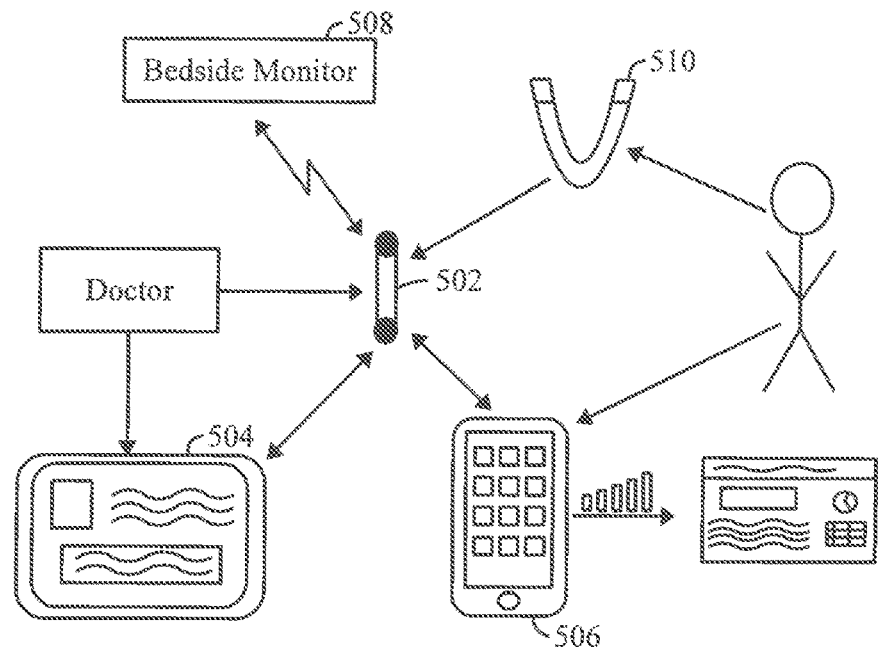
FIG. 5 illustrates a system level diagram indicating potential devices and networks in which the methods and systems herein may be utilized in accordance with embodiments herein.

FIG. 5 illustrates a system level diagram indicating potential devices and networks that utilize the methods and systems herein. For example, an implantable cardiac monitoring device (CM) 502 may be utilized to collect a cardiac activity data set. The ICM 502 may supply the CA data set (CA signals and DD feature markers) to various local external devices, such as a tablet device 504, a smart phone 506, a bedside monitoring device 508, a smart watch and the like. The devices 504-508 include a display to present the various types of CA signals, markers, statistics, diagnostics and other information described herein. The ICM 502 may convey the CA data set over various types of wireless communications links to the devices 504, 506 and 508. The ICM 502 may utilize various communications protocols and be activated in various manners, such as through a Bluetooth, Bluetooth low energy, WiFi or other wireless protocol. Additionally or alternatively, when a magnetic device 510 is held next to the patient, the magnetic field from the device 610 may activate the ICM 502 to transmit the cardiac activity data set and AF data to one or more of the devices 504-508.

The processes described herein for analyzing the cardiac activity data and/or confirm AF detection may be implemented on one or more of the devices 504-508. Additionally or alternatively, the ICM 502 may also implement the confirmatory processes described herein. The devices 504-508 may present the CA data set and AF detection statistics and diagnostics to clinicians in various manners. As one example, AF markers may be illustrated on EGM signal traces. AF and sinus markers may be presented in a marker channel that is temporally aligned with original or modified CA signals. Additionally or alternatively, the duration and heart rate under AF may be formatted into histograms or other types of charts to be presented alone or in combination with CA signals.

Figure 6:
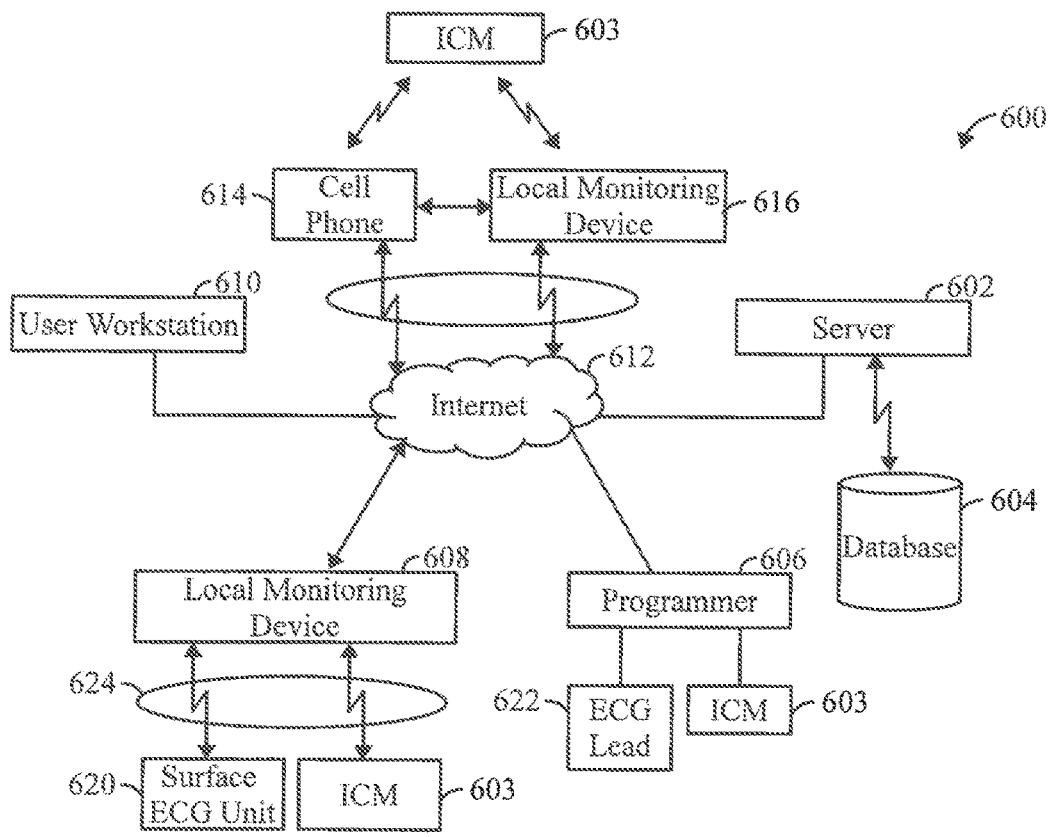
FIG. 6 illustrates a distributed processing system in accordance with embodiments herein.

FIG. 6 illustrates a distributed processing system 600 in accordance with embodiments herein. The distributed processing system 600 includes a server 602 connected to a database 604, a programmer 606, a local monitoring device 608 and a user workstation 610 electrically connected to a network 612. Any of the processor-based components in FIG. 6 (e.g., workstation 610, cell phone 614, local monitoring device 616, server 602, programmer 606) may perform the processes discussed herein.

The network 612 may provide cloud-based services over the internet, a voice over IP (VoIP) gateway, a local plain old telephone service (POTS), a public switched telephone network (PSTN), a cellular phone based network, and the like. Alternatively, the communication system 612 may be a local area network (LAN), a medical campus area network (CAN), a metropolitan area network (MAN), or a wide area network (WAN). The communication system 612 serves to provide a network that facilitates the transfer/receipt of data and other information between local and remote devices (relative to a patient). The server 602 is a computer system that provides services to the other computing devices on the network 612. The server 602 controls the communication of information such as cardiac activity data sets, bradycardia episode information, asystole episode information, AF episode information, markers, cardiac signal waveforms, heart rates, and device settings. The server 602 interfaces with the network 612 to transfer information between the programmer 606, local monitoring devices 608, 616, user workstation 610, cell phone 614 and database 604. The database 604 stores information such as cardiac activity data, AF episode information, AF statistics, diagnostics, markers, cardiac signal waveforms, heart rates, device settings, and the like, for a patient population. The information is downloaded into the database 604 via the server 602 or, alternatively, the information is uploaded to the server 602 from the database 604. The programmer 606 may reside in a patient's home, a hospital, or a physician's office. The programmer 606 may wirelessly communicate with the ICM 603 and utilize protocols, such as Bluetooth, GSM, infrared wireless LANs, HIPERLAN, 3G, satellite, as well as circuit and packet data protocols, and the like. Alternatively, a telemetry "wand" connection may be used to connect the programmer 606 to the ICM 603. The programmer 606 is able to acquire ECG from surface electrodes on a person (e.g., ECGs) 622, electrograms (e.g., EGM) signals from the ICM 603, and/or cardiac activity data, AF episode information, AF statistics, diagnostics, markers, cardiac signal waveforms, atrial heart rates, device settings from the ICM 603. The programmer 606 interfaces with the network 612, either via the Internet, to upload the information acquired from the surface ECG unit 620, or the ICM 603 to the server 602.

The local monitoring device 608 interfaces with the communication system 612 to upload to the server 602 one or more of cardiac activity data set, AF episode information, AF statistics, diagnostics, markers, cardiac signal waveforms, heart rates, sensitivity profile parameter settings and detection thresholds. In one embodiment, the surface ECG unit 620 and the ICM 603 have a bi-directional connection 624 with the local RF monitoring device 608 via a wireless connection. The local monitoring device 608 is able to acquire cardiac signals from the surface of a person, cardiac activity data sets and other information from the ICM 603, and/or cardiac signal waveforms, heart rates, and device settings from the ICM 603. On the other hand, the local monitoring device 608 may download the data and information discussed herein from the database 604 to the surface ECG unit 620 or the ICM 603.

The user workstation 610 may be utilized by a physician or medical personnel to interface with the network 612 to download cardiac activity data and other information discussed herein from the database 604, from the local monitoring devices 608, 616, from the ICM 603 or otherwise. Once downloaded, the user workstation 610 may process the CA data in accordance with one or more of the operations described above. The user workstation 610 may upload/push settings (e.g., sensitivity profile parameter settings), ICM instructions, other information and notifications to the cell phone 614, local monitoring devices 608, 616, programmer 606, server 602 and/or ICM 603. For example, the user workstation 610 may provide instructions to the ICM 603 in order to update sensitivity profile parameter settings when the ICM 603 declares too many false AF detections.

The processes described herein in connection with analyzing cardiac activity data for confirming or rejecting AF detection may be performed by one or more of the devices illustrated in FIG. 6, including but not limited to the ICM 603, programmer 606, local monitoring devices 608, 616, user workstation 610, cell phone 614, and server 602. The process described herein may be distributed between the devices of FIG. 6.

Figure 7:
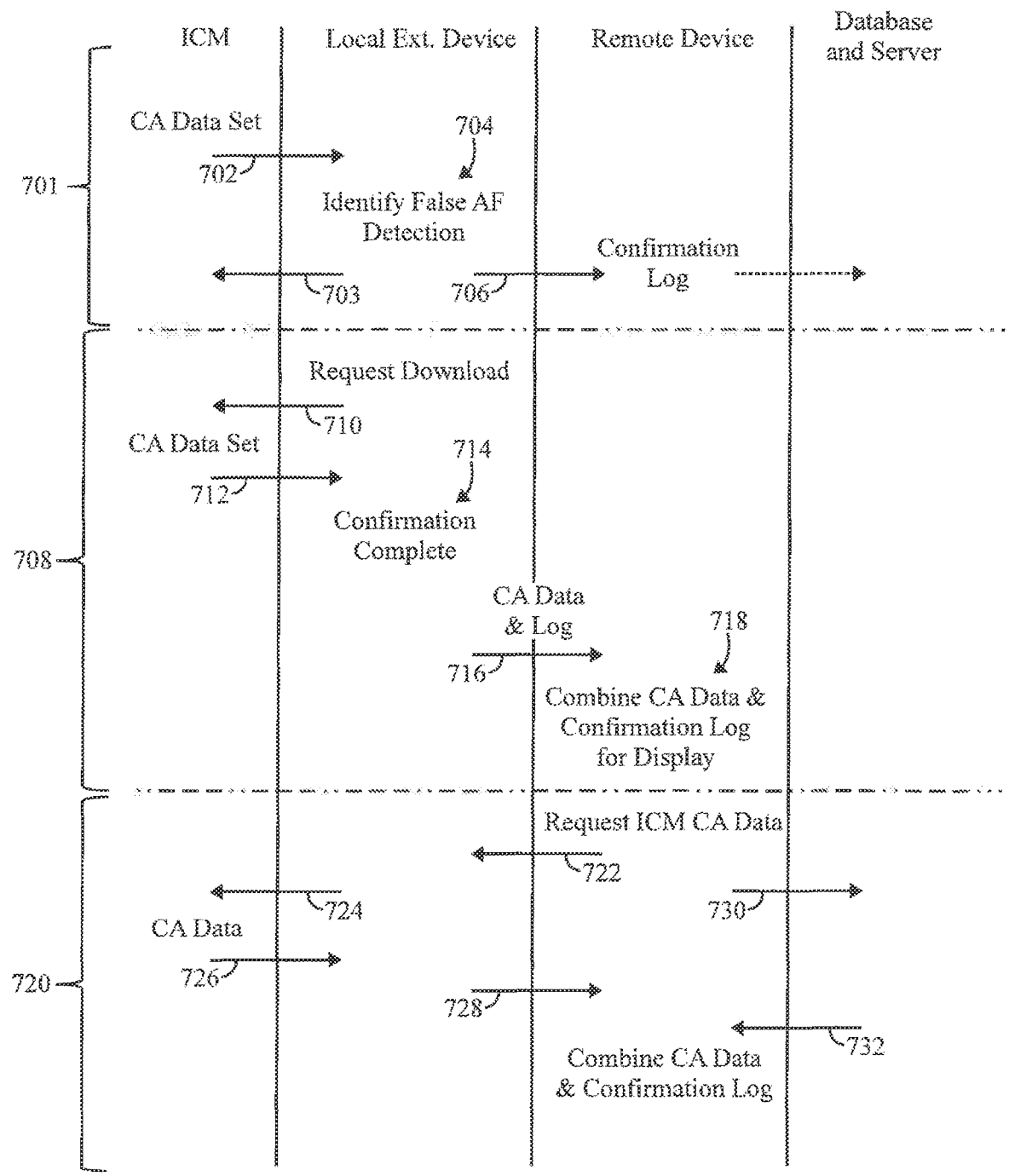
FIG. 7 illustrates a collection of communications between the ICM, a local device, a remote device and a server/database in accordance with embodiments herein.

FIG. 7 illustrates examples of communication sessions between the ICM, a local external device, a remote device and a server/database in accordance with embodiments herein. For convenience, reference is made to the devices of FIGS. 5 and 6, in connection with FIG. 7. For example, the local device may represent a cell phone 614, smart phone 506, bedside monitor 508 or local monitoring device 608, 616, while the remote device may represent a workstation 610, programmer 606, or tablet device 504.

During an AF detection and confirmation session 701, at 702, an ICM 100 provides a CA data set to a local device. At 704, the local device utilizes the EFR and confirmatory feature detectors processes described herein to analyze at least a portion of the CA signals to identify false AF detection. The false AF detections are used to generate or update a confirmation log 706. As described herein, the confirmation log 706 may include a log of the "false positive" episode counts from the original CA data set. The confirmation log 706 may also include corrective characterizations of individual events that were mischaracterized in the original CA data.

In certain instances, it may be desirable to return the confirmation log 706 information to the ICM as denoted at 703. In certain implementations, an ICM is provided with certain security features that prevent an external device (e.g., cell phone or local monitoring device) from directly changing sensitivity profile parameter settings and/or writing to any or at least certain sections of the memory within the ICM. For example, the security features may prevent an external device from writing over-sensitivity profile parameter settings and/or over the AF statistics and diagnostics that are generated and stored on the ICM.

Optionally, as a workaround, at 703, the confirmation log 706 may be written to a more flexible section of memory within the ICM (also referred to as an external device accessible section), along with header and/or metadata information tying the confirmation log 706 to a particular portion of the CA data. Additionally or alternatively, at 704, the local external device may pass the confirmation log 706 to one or more remote devices and optionally to the database and server. The confirmation log 706 may be written to memory of an external device that interacts directly and regularly with the ICM, such as cell phone 614, local monitoring device 608, 616 and the like. The confirmation log 706 may be associated with particular CA data sets, such as based on time of data acquisition.

Optionally, a remote pairing session 708 may be performed between CA data on an ICM and locally externally stored confirmation logs. For example, the local external device may be directed to initiate a data transfer/download from the ICM, such as at 710, at a point in time separate from and after performing the AF detection confirmation processes described herein. The local external device receives the CA data set at 712 and determines, at 714, that the CA data set has already been analyzed to confirm AF detection. At 716, the local external device identifies a confirmation log stored at the local external device that corresponds to the CA data set, and at 716, appends the confirmation log to the associated CA data set, such as based on time of data acquisition. The cumulative information of the CA data set and confirmation log are transferred, through the external device, to a remote server 602, database 604, workstation 610, programmer 606 or otherwise.

By maintaining the confirmation log, for a particular CA data set at the local external device in association with the original CA data set, remote devices (e.g., programmer 606, server 602, etc.) receive and process both the original CA data set and the confirmation log. The remote device obtains the "traditional" device diagnostic sections, and is also afforded additional information from the confirmation log and is able to account (at 718) for cumulative adjustments/adjudications in AF detection before displaying a consolidated set of AF statistics and diagnostics to a physician or medical personnel.

Additionally or alternatively, the operations of FIG. 7 may be implemented in connection with remotely stored confirmation logs, such as in communication sessions 720. At 722, a remote device may request CA data from a particular ICM by conveying a corresponding request to a local external device associated with the corresponding ICM. The local external device forwards the data request, at 724, to the ICM, in response thereto, at 726, the ICM transmits the CA data set to the local external device. The local external device forwards the CA data set, at 728, to the remote device. Optionally, before relaying the CA data set, at 728, the local external device may first determine whether the CA data set has first been analyzed for AF detection confirmation. In the example at 720, it is presumed that the CA data set has already been analyzed for AF detection confirmation and thus the local external device need not perform the confirmation analysis at this time. Additionally or alternatively, the remote device may include, in the request, a direction to the local external device to not perform AF detection confirmation (e.g., the remote device knows that in AF detection confirmation has already been performed and stored elsewhere).

In connection with or separate from the request for CA data set at 722, the remote device conveys a request, at 730, to a server and database for any confirmation logs related to the requested CA data set. The requested may be broadcast to multiple external devices on the network or directed to a particular server/database known to maintain information in connection with the particular ICM. Additionally or alternatively, the remote device may hold the request, at 730, until after receiving the CA data set, at 728. For example, once a remote device receives the CA data set, at 728, the remote device may include, within the request for confirmation logs, an indication of the time and date at which the CA data set was collected. In response to the request, the server and database return, at 732, one or more confirmation logs (if present). Thereafter, the remote device combines the CA data set and confirmation log to present a consolidated summary of the data to a physician or other medical personnel.

In connection with embodiments herein, the cloud-based approach allows an AF episode that is detected by the ICM using the traditional detection algorithms, to be passed through the local external device and stored at the server 602, database 604, workstation 610 or at another remote device within the cloud-based system. When an individual ICM is interrogated for a CA data set, the interrogation device would also request, from the cloud-based system, any additional information, such as any confirmation logs stored elsewhere within the system. For example, when an external device, such as a cell phone 614, local monitoring device 608, 616 and/or programmer 606 interrogate an individual ICM, the cell phone 614, local monitoring device 608, 616 and/or programmer 606 would also broadcast an ICM data supplement request over the cloud-based system. The ICM data supplement request requests additional data/information related to the individual ICM (e.g., based on the ICM serial number). In response thereto, the server 602 and/or other remote system may provide, to the requesting device, one or more confirmation logs or other information regarding past operation of the ICM. The requesting device then combines the CA data set from the ICM with related data (e.g., a confirmation log associated with a particular AF episode and/or group of cardiac events) from an external source. The external devices pulls data from the cloud in connection with ICM interrogation, and combine the CA data from the ICM with any corrective or confirmation data from the log, before presenting a consolidated data summary to a physician or medical personnel.

III. P-Wave Detection Process

Figure 8A:
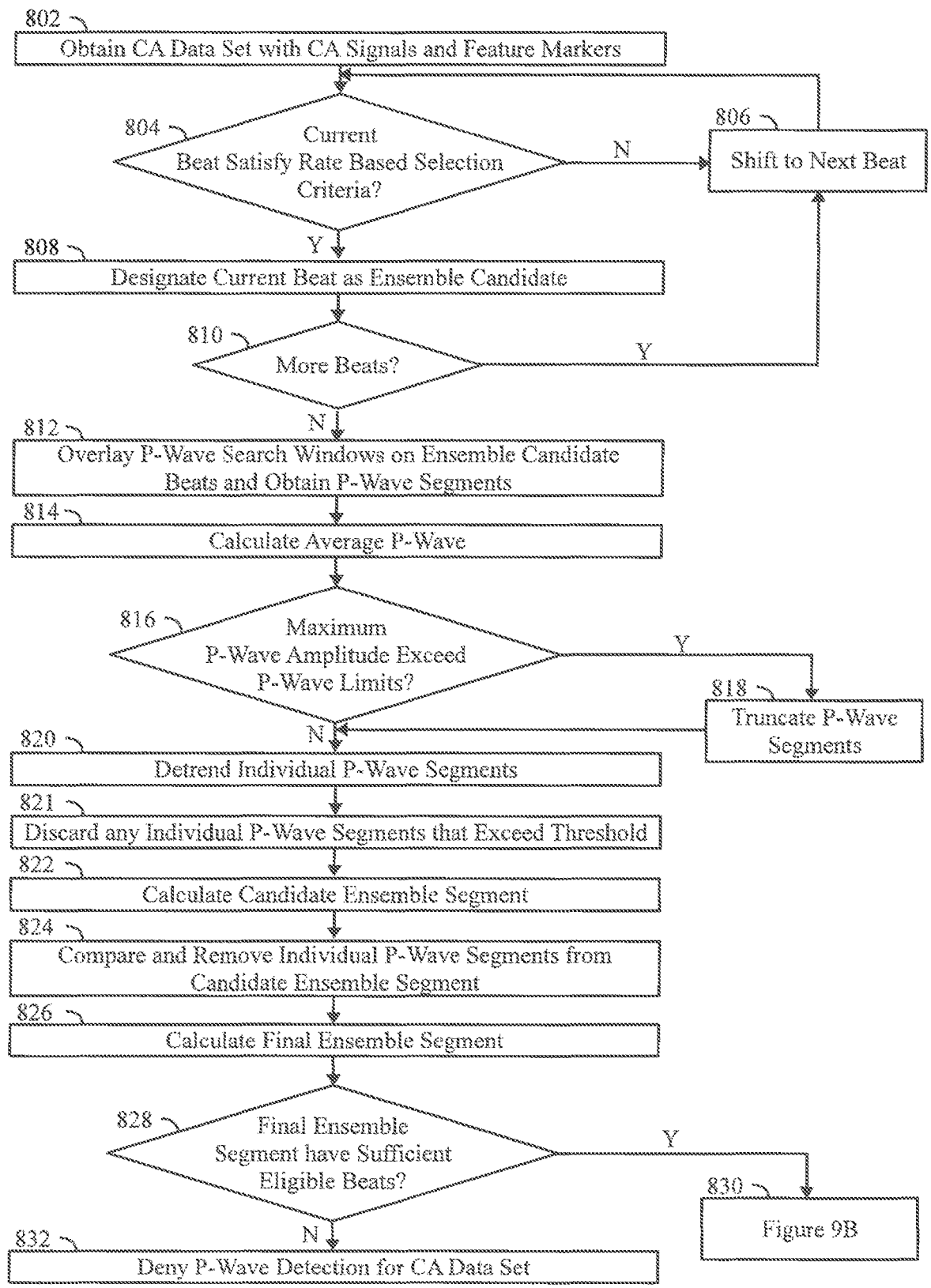
FIG. 8A illustrates a block diagram of a P-wave detection process implemented in accordance with embodiments herein.

FIG. 8A illustrates a block diagram of a P-wave detection process implemented in accordance with embodiments herein. Prior to the P-wave detection process, the CA signals are analyzed by an implanted device for sinus and/or arrhythmia features/episodes. The CA signals have been appended with a marker channel that includes features markers (e.g., sinus and/or arrhythmia markers such as R-wave markers, AF markers, etc. annotated by the implanted device). The feature markers are stored in connection with the CA signals to form a CA data set. The feature markers may be identified in connection with an arrhythmia detection process that is implemented by the ICM, by a local external device and/or by a remote server. At, 802 one or more processors obtain the CA data set with the CA signals and feature markers. For example, when the P-wave detection process may be implemented in real time by an ICM, the processors may receive the CA data set in real time from an onboard R-wave detection process. Additionally or alternatively, while still implemented on the ICM, the P-wave detection process may obtain the CA data set from a section of memory in the ICM, and analyze the CA data set for P-waves, such as in connection with an arrhythmia first pass detection process or second pass confirmation process. Additionally or alternatively, the P-wave detection process may be implemented on a local external device (e.g., patient smart phone, tablet device, laptop computer) while or after a CA data set is downloaded from an ICM. When implemented on a local external device, the P-wave detection process may analyze the CA data set for P-waves in connection with an arrhythmia confirmation process that updates the CA data set before transmitting a modified CA data set to a remote server. Additionally or alternatively, the P-wave detection process may be implemented at a remote server while the remote server is performing an arrhythmia confirmation process upon a CA data set received from an ICM and/or local external device.

At 804, the one or more processors obtain a current beat from the CA signals and determine whether the current beat satisfies a rate based selection criteria, such as an RR interval rate criteria in which a beat is disregarded when the RR interval is outside of a predetermined range. The processors declare the current beat, from the CA signals, to be an eligible (also referred to as a candidate) beat or an in-eligible beat based on whether the current beat satisfies the rate based selection criteria. When the current beat satisfies the rate based selection criteria, flow continues to 808. When the rate based selection criteria are not satisfied, flow moves to 806, where a search window is shifted to a next candidate beat that is analyzed at 804. When the rate based selection criteria are not satisfied at 804, the current beat is disregarded and a P-wave segment therein is not included within a subsequent ensemble. The determination at 804 is applied to avoid potentially including PVCs or other abnormal sensed beats (e.g., long RR interval due to under-sensing or short RR interval due to over-sensing of T wave) within a P-wave ensemble (formed as explained hereafter). Including PVCs or abnormal beats can lead to an undue bias in the P-wave ensemble (e.g., ensemble average), and can ultimately potentially lead to false P-wave detection. Accordingly, the operation at 804 is selective in determining which beats and candidate segments are appropriate to add to an ensemble generator and to form the basis for a P-wave segment ensemble.

By way of example, the rate based beat selection criteria may represent a RR interval rate criteria that applies a two-part selection test. For example, as a first part of the rate based selection criteria, the processors determine whether the RR interval of the current beat from the previous beat is within a predetermined interval range (e.g., 600 to 1500 ms). As a second part of the rate based selection criteria, the processors determine whether the RR interval of current beat is greater or shorter than the RR interval of previous beat, and if shorter, whether the difference in RR intervals is within a range (e.g., 100 ms). For example, when the current beat RR interval is 600 ms and the previous beat RR interval is 920 ms, the current beat is shorter, but differs by more than 100 ms from the previous beat and thus would not satisfy the second part of the rate based selection criteria. Alternatively, the difference can be a percentage of the previous RR interval (e.g., 20%). As the same example described above, the current beat RR interval is shorter than the previous interval by 35% thus would not satisfy the criteria.

Figure 9:
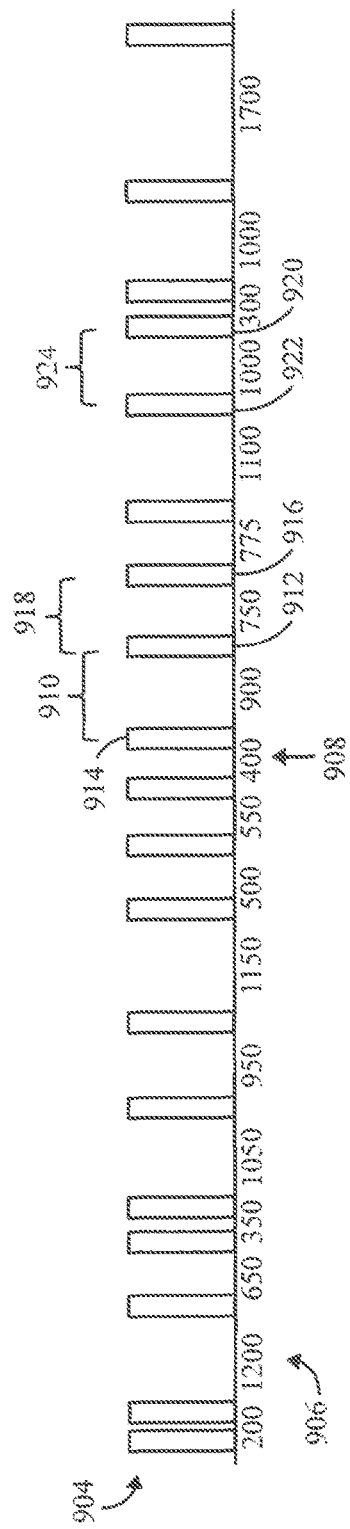
FIG. 9 illustrates a series of feature markers associated with cardiac events to further describe an example for applying the two-part test for rate based selection criteria in accordance with an embodiment herein.

FIG. 9 illustrates a series of feature markers associated with cardiac events to further describe an example for applying the two-part test for rate based selection criteria in accordance with an embodiment herein. The feature markers of FIG. 9 represent R-wave markers 904 that are separated by RR intervals 906 and that include an AF detection trigger 908. In the present example, the process of FIG. 8A analyzes candidate segments following the AF detection trigger 908. Optionally, the process of FIG. 8A may analyze candidate segments before or without regard for the AF detection trigger 908. Following the AF detection trigger 908, the P-wave search window is overlaid upon a first candidate segment 910 that is defined to correspond to a predetermined time duration preceding the R-wave marker 912. The R-wave marker 912 occurred 900 ms following the preceding R-wave marker 914 which occurred 400 ms after the preceding R-wave marker. The current beat, associated with R-wave marker 912, satisfies part one of the rate based selection criteria as the RR interval of 900 ms is within the predetermined range of 600-1500 ms. The current beat for the R-wave marker 912 also satisfies part two of the rate based selection criteria as the RR interval of 900 ms is longer than the preceding RR interval (400 ms) of the previous beat 914. Thus, the candidate segment 910 would be included within the P-wave segment ensemble.

Moving forward to the next R-wave marker 916, the corresponding RR interval is 750 ms which falls within the predetermined range of 600 to 1500 ms. The RR interval of 750 ms is shorter than the RR interval (900 ms) for the previous beat corresponding to marker 912. Thus, the second part of the rate based selection criteria must be further analyzed to determine whether the RR intervals associated with the beats for R-wave markers 912 and 916 are within the acceptable range of one another. The RR interval of 750 is 150 ms shorter than the RR interval of 900 ms and thus the second part of the rate based selection criteria fails. Consequently, the process of FIG. 8A would exclude the P-wave candidate segment 918 corresponding to the beat associated with R-wave marker 916.

As one further example, consider the beat associated with marker 920. The beat for marker 920 has an RR interval of 1000 ms, falling within the range for the first part of the test. The RR interval of 1000 ms is less than the RR interval of 1100 ms for the preceding beat (corresponding to marker 922). Therefore, the second part of the test is applied and the process determines that the RR interval of 1000 ms for the beat (corresponding to marker 920) is within 100 ms of the RR interval of 1100 ms for the previous beat (corresponding to marker 922). Thus, the second part of the test passes and the P-wave candidate segment 924 from with the beat (corresponding to marker 920) is included within the ensemble generator.

Returning to FIG. 8A, at 808, the one or more processors designate the current beat as an eligible or candidate beat to be potentially added to the segment ensemble of P-waves. At 810, the one or more processors determine whether a sufficient number of beats have been added to the list of ensemble candidate beats. For example, the operations at 804-810 may repeat until 10, 20 or another desired number of beats have been added to the list of ensemble candidate beats. The number of candidates beats (and candidate P-wave segments) used may vary depending on various criteria, such as rate-dependent duration and/or quality of the P-wave segments (and/or R-wave segments) in the beats. For example, at 810, the processors may analyze the quality (e.g., signal-to-noise ratio, energy content, number of peaks and valleys) and based thereon determine to include additional or fewer candidates beats/segments in the ensemble. As another example, when utilizing duration, the processors may determine a first number of candidates beats/segments (e.g., 8) when the heart rate is relatively slow (e.g., 70 bpm), and may determine a second number of candidates beats/segments (e.g., 16) when the heart rate is relatively fast (e.g., 100 bpm). When more beats are to be added to the ensemble, flow moves from 810 back to 806. Otherwise, flow continues to 812.

At 804-810, the processors may step through the arrhythmia episode, as designated by the markers within the CA data set, and only utilize candidate beats overlapping or following an arrhythmia episode trigger. For example, the processors may apply the P-wave detection process of FIG. 8A to beats following an AF detection trigger/marker. Once an AF detection trigger is identified, the P-wave detection process herein may be applied to a series of beats following the AF detection trigger to confirm a point at which the AF episode terminates. Additionally or alternatively, the processors may begin at a beginning of the CA data set and step through each cardiac event therein beat by beat. Once a desired number of ensemble candidate beats or minimum required number of candidate beats within a duration window are identified, flow moves to 812.

At 812, the one or more processors overlay a P-wave search window onto a candidate segment within each of the candidate beats to obtain candidate P-wave segments. To position the P-wave search window, the processors use device declared R wave marker in a corresponding beat to use as a reference point. The P-wave search window is defined to overlay CA signals at a predetermined time before or after the reference feature marker. For example, when an R-wave marker is utilized as the reference feature marker, a P-wave search window may be positioned to overlap a candidate segment that precedes the R-wave marker by a predetermined time, such as a range beginning 75 ms before the R-wave marker and continuing to a point 300 ms before the R-wave marker, thereby defining a P-wave search window that is proximately 225 ms long. It is recognized that the start and end points, and the duration, for the P-wave search window may be varied. At 812, the one or more processors copy P-wave segments from each of the ensemble candidate beats.

At 814, the one or more processors combined the candidate P-wave segments through a predetermined mathematical function, such as averaging to form a P-wave combination.

At 816, the one or more processors analyze the P-wave combination to determine a signal characteristic of interest from the P-wave combination (e.g., a maximum signal amplitude), such as to remove outliers. At 816, the one or more processors determine whether the signal characteristic of interest from the P-wave combination exceeds one or more P-wave limits. For example, the maximum signal amplitude may be compared to a voltage threshold (e.g., 0.1 mV). Additionally or alternatively, the processors may identify a location of the maximum signal amplitude within the P-wave combination and determine whether the maximum signal amplitude occurs too close to (e.g., within 40 ms of an end of the P-wave average). When the maximum signal amplitude exceeds the voltage threshold and/or occurs too close in time to an end of the P-wave average, the processors may declare the maximum P-wave amplitude to exceed expected P-wave limits. When the P-wave limits are exceeded, flow moves to 818. When the P-wave limits are not exceeded, flow moves to 820.

The P-wave limit analysis at 816 is applied to determine whether a portion of an R-wave is mistakenly included within the P-wave search window and thus could potentially be treated as part of the candidate P-wave segments that later form the P-wave segment ensemble. To avoid including portions of the R wave within the P-wave segment ensemble, the processors truncate, at 818, a predetermined trailing duration from each of the candidate P-wave segments (e.g., the last 40 ms). By shortening the candidate P-wave segments, the operations at 816, 818 avoid undue R-wave influence upon the P-wave detection operations herein. Next, flow moves from 818 to 820.

At 820, the one or more processors applies a de-trending operation to remove baseline drift from each of the individual P-wave segment. For example, initial and final coordinates of a P-wave segment may be defined by voltage levels, where the initial and final coordinates have corresponding voltage levels. When baseline drift is not present, it would be expected that the initial and final coordinates of an individual P-wave segment have approximately similar voltage levels. However, when the final coordinate has a voltage level that is greater than or less than the voltage level of the initial coordinate, the difference is called a baseline drift. The processors remove baseline drift by first constructing a straight line (referred to as a drift line) using the initial and last coordinates of a corresponding P-wave segment. The drift line is subtracted from the P-wave segment to obtain a "de-trended" (or drift adjusted) P-wave segment.

At 821, the one or more processors discard any individual beat that has a P-wave segment that exceed a P-wave threshold. For example, for each individual beat, the processors calculate an absolute maximum for the corresponding individual P-wave segment and compare the absolute maximum to a P-wave threshold (e.g., 0.1 mV). When the absolute maximum for any individual P-wave segment exceeds the P-wave threshold, the individual beat (associated with the overly large P-wave segment) is removed or discarded, thereby leaving a subset of beats in the CA data set. The discarded beat is no longer used in the ensemble calculated at 822, to avoid corrupting the ensemble with any beats that have very noising signals.

Next, at 822, the one or more processors calculate a P-wave segment ensemble by combining the de-trended P-wave segments (and segments that were not discarded) based on a predetermined mathematical function. The P-wave segment ensemble may be formed by applying a non-weighted or weighted averaging between the individual P-wave segments as well as applying additional or alternative mathematical functions.

At 824, the one or more processors compare the individual P-wave segments to the P-wave segment ensemble utilizing a desired mathematical comparison function. For example, the correlating may correlate a first P-wave segment, for a first beat from the ensemble of candidate beats, with the P-wave segment ensemble for the ensemble of candidate beats for morphology similarity analysis. The processors determine whether the individual P-wave segments exhibit a desired level of match or correlation to the P-wave segment ensemble (e.g., a match occurs when correlation exceeds a correlation coefficient threshold of 0.85). The processors remove, from the P-wave segment ensemble, any individual P-wave segments that do not exhibit the desired level of match or correlation to the P-wave segment ensemble.

At 826, the one or more processors calculate a final P-wave segment ensemble (e.g., final average) based on a collection of eligible beats formed by the remaining eligible beats/individual P-wave segments. At 828, the one or more processors determine whether a sufficient number of individual P-wave segments were utilized to form the final P-wave segment ensemble. For example, it may be desired to have at least eight beats within the P-wave segment ensemble (e.g., from approximately a 20 second EGM strip). When the P-wave segment ensemble includes at least the desired number of eligible beats, flow moves to 830. Otherwise, flow moves to 832 where the process denies P-wave detection for the current CA data set and the process ends. P-wave detection is denied at 832 as the processors determined that there is insufficient evidence of a consistent P-wave within the CA data set.

Figure 8B:
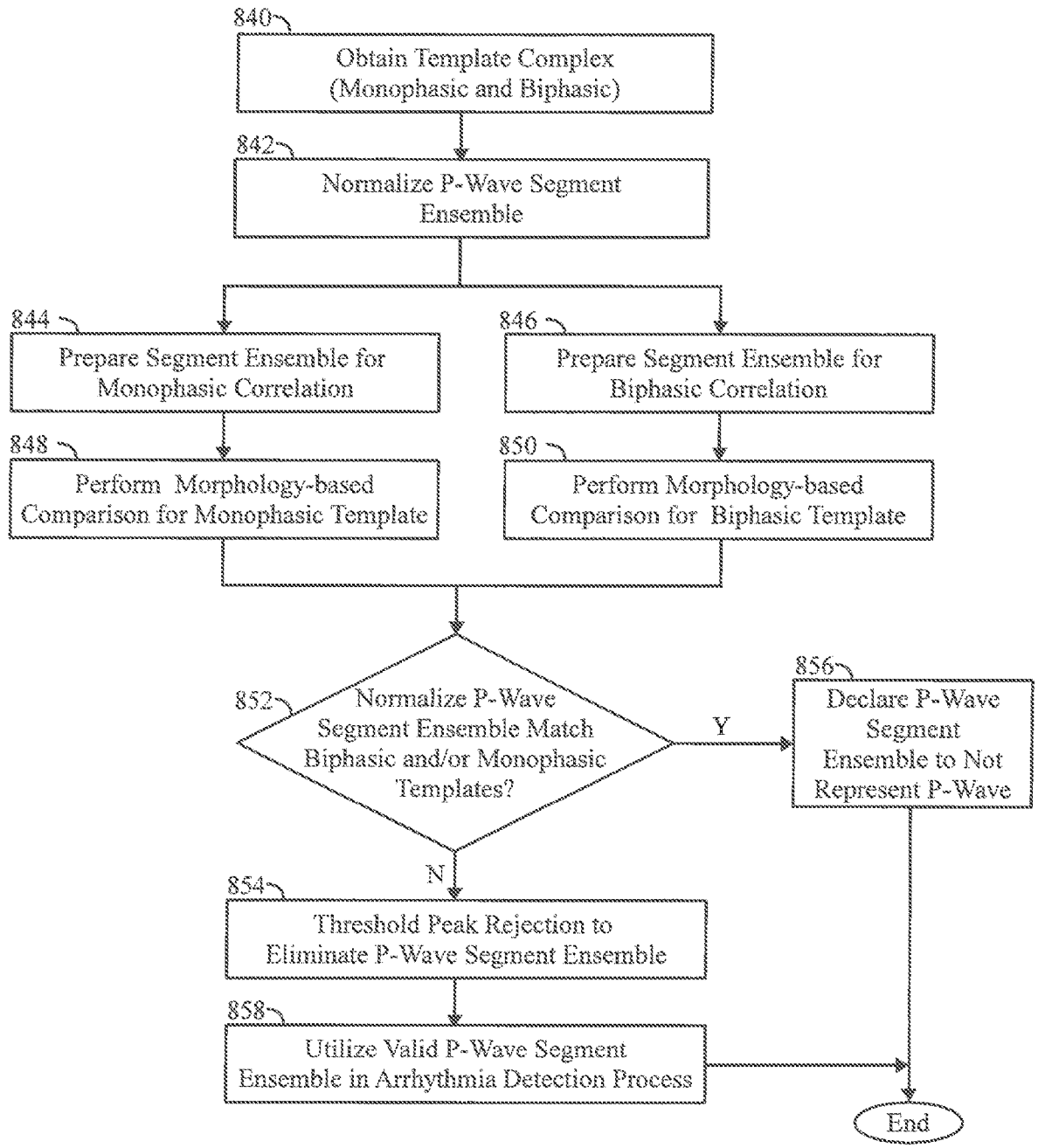
FIG. 8B illustrates a peak selection and P-wave detection process implement it in accordance with embodiments herein.

At 830, the process moves onto a peak selection and P-wave detection process as described hereafter in connection with FIG. 8B.

FIG. 8B illustrates a peak selection and P-wave detection process implement it in accordance with embodiments herein. The operations of FIG. 8B are performed after the process of FIG. 8A when it is determined that sufficient beats were used to establish the P-wave segment ensemble for the current CA data set. The process of FIG. 8B applies a P-wave detector to extract and confirm a P-wave from the segment ensemble. A morphology-based comparison is used to confirm that the morphology of the extracted P-wave matches an expected P-wave morphology.

At 840, the one or more processors obtain a template complex that is stored in memory. The template complex was generated prior to collection of the present CA data set being analyzed. The template complex may be generated based on prior CA signals from the present patient and/or from a patient population. The template complex includes two or more P-wave template clips, where one clip corresponds to a monomorphic P-wave and the other clip correspond to a biphasic P-wave. In the mono phasic P-wave, the phase is always positive or always negative. The biphasic P-wave, the signal transitions between a positive phase leading a negative phase. When generating the P-wave template dips, CA signals for the present patient or patient population were processed by the operations of FIG. 8A to perform rate based beats selection and ensemble averaging as described above in connection with FIG. 8A. The P-wave template clips are also normalized to extend between a range of zero and one, while maximum peaks within the P-wave template clips are extracted. Each P-wave template clip may be defined based on a predetermined number of correlation points (e.g., 20 correlation points). By way of example, the correlation points may be defined as follows. For the monophasic template, the first two and the last two correlation points are padded with zeros. The correlation points X-Y are defined as follow: Mono_Template (X:Y)=Clip_Signal (peak_pos−X:peak_pos+Y), where Mono_Template is the monophasic template vector, Clip_Signal is the ensemble average of the clip being considered for template generation and peak_pos is the position of the peak extracted from the ensemble average.

For the biphasic template, the correlation points were defined as follows: Bi_Template (X:Y)=Clip_Signal (peak_posX:peak_posY), where Bi_Template is the biphasic template vector, Clip_Signal is then stumble average of the clip being considered for template generation and peak_pos is the position of the positive peak extracted from the ensemble average.

Figure 10:
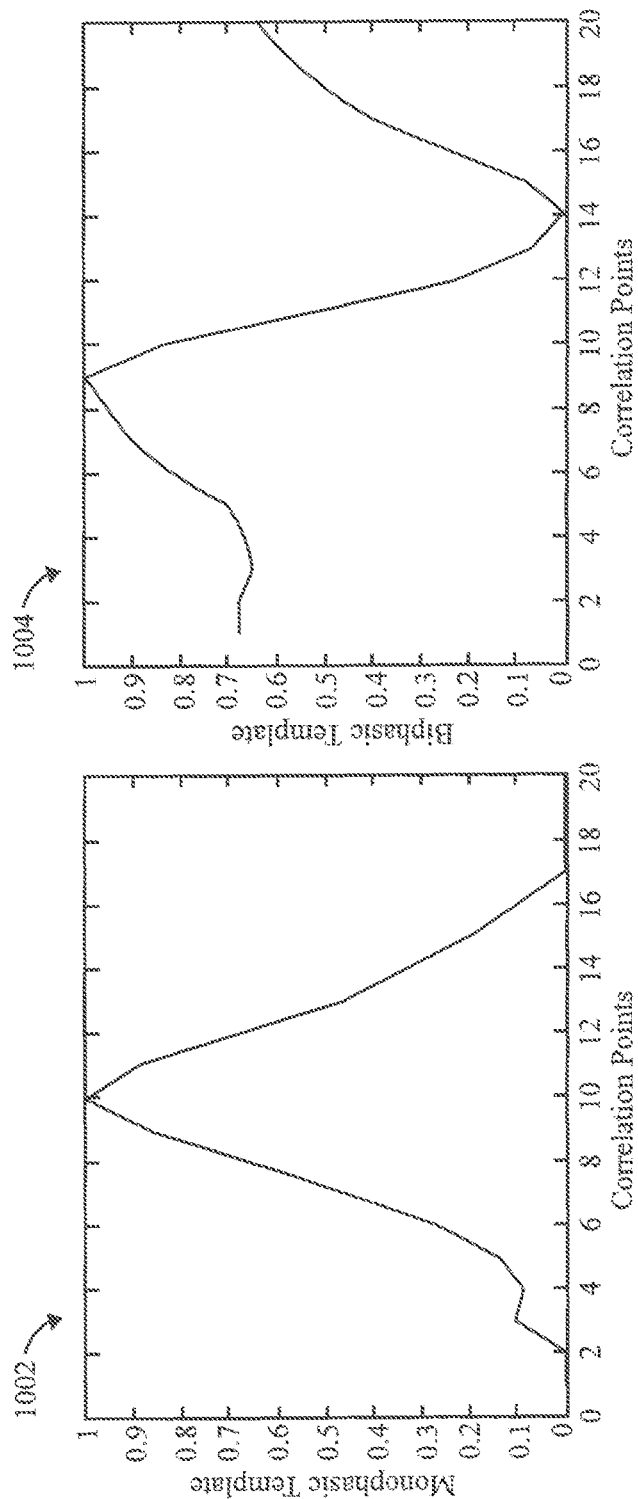
FIG. 10 illustrates an example of P-wave template clips that may be utilized in accordance with embodiments herein.

FIG. 10 illustrates an example of P-wave template clips that may be utilized in accordance with embodiments herein. A monomorphic template 1002 and a biphasic template 1004 are shown to be normalized between values of zero and one and to be defined in connection with 20 correlation points.

Returning to FIG. 8B, at 842, the one or more processors normalize the P-wave segment ensemble (calculated in connection with FIG. 8A). For example, the normalization operation may be performed utilizing the calculation of: Norm_signal=Ens_signal−min(Ens_signal)/((max(Ens_signal)−min(Ens_signal)), where Norm_signal is the resultant normalized signal, Ens_signal is the P-wave segment ensemble, max(Ens_signal) is the maximum within the P-wave segment ensemble and min(Ens_signal) is the minimum within the P-wave segment ensemble.

At 844 and 846, the one or more processors perform a phase determination for the P-wave segment ensemble to ensure an accurate comparison with the monophasic and/or biphasic templates. At 844, for comparison with the monophasic template, the processors find a peak of the normalized P-wave segment ensemble and a peak of an inverted P-wave segment ensemble. The peaks of the normalized and inverted P-wave segment ensembles are compared. If the peak of the original P-wave segment ensemble is smaller than a peak of the inverted signal, the ensemble segment is inverted. At 846, for comparison with the biphasic template, the processors find the positive and negative peaks of the normalized segment ensemble. If the positive peak of the normalized segment ensemble trails the negative peak, the signal is inverted.

At 848 and 850, the one or more processors perform a morphology-based comparison between the segment ensembles prepared at 844, 846 and the corresponding monophasic and biphasic morphology templates, respectively. For example, the morphology-based comparison may include performing a point correlation between the segment ensembles prepared at 844, 846 and the corresponding monophasic and biphasic morphology templates, respectively. More specifically, at 848, the processors perform a monophasic morphology comparison in which the first two and the last two correlation points are padded with zeros. The rest of the correlation points are defined as follows: Mono_Correlation(X:Y)=Norm_Signal(peak_posX:peak_posY), where Mono_Correlation is the monophasic ensemble vector (e.g., monophasic template 1002 in FIG. 10), Norm_Signal is the normalized segment ensemble of the present CA data set being considered for P-Wave detection and peak_pos is the position of the peak extracted from the segment ensemble.

It is recognized that the foregoing process at 848, 850 may be performed utilizing other morphology-based comparisons such as statistical approaches (e.g., signal strength, Kendal Tau and the like).

At 850, the processors perform a biphasic morphology comparison in which correlation points are defined based on a biphasic template, normalized segment ensemble, and a difference in the lengths of the biphasic morphology template and the normalized segment ensemble.

At 852 the one or more processors separately correlate the normalized P-wave segment ensemble with each of the monophasic and biphasic templates (FIG. 10). A match is determined when the P-wave segment ensemble and at least one of the monophasic or biphasic templates satisfy a correlation threshold. When a match occurs with either of the biphasic and/or monophasic templates, the process determines that a valid P-wave is present and flow branches to 854. When a match does not occur between the P-wave segment ensemble and either of the biphasic and/or monophasic templates, flow branches to 856. At 856, the one or more processors declare the normalized P-wave segment ensemble to not include a P-wave. At 856, the processors do not identify a P-wave in the current CA signals being analyzed. In accordance with at least some embodiments, at 856, the processors may leave the current CA signals as unclassified, thereby indicating that insufficient information exist to identify specific P-waves. Alternatively, the operation at 856 may declare the current CA signal to not include a P-wave.

At 854, the one or more processors perform a threshold peak rejection wherein a threshold based criteria is used to eliminate any P-waves detected that fall below a predetermined threshold. For example, the processors may apply a voltage threshold (e.g., 10 uV) and determine that a valid P-wave is present when the P-wave segment ensemble has a peak that exceeds the voltage threshold. The processors may reject any P-wave segment ensemble that has a peak below the voltage threshold as such low voltage peaks are not considered indicative of a valid P-wave. Additionally or alternatively, the one or more processors may update the monophasic and/or biphasic templates on a regular basis (e.g., daily, weekly, monthly) based on valid P-waves that are detected in accordance with the process of FIGS. 8A and 8B.

At 858, the one or more processors utilize the valid P-wave in an arrhythmia detection process (e.g., the ORI process of FIG. 2A, and or the confirmatory AF detection process of FIGS. 3 and 4) to determine at least one of an arrhythmia entry, arrhythmia presence or arrhythmia exit. For example, the positive presence of a P-wave would prevent the AF detection process from entering an AF state ("AF entry"), even if another AF index indicates that AF is present (e.g., AF combined probability and Sudden Onset criteria of a traditional AF detection process). The positive presence of the P-wave may prevent entry into an AF state until the AF process internal state is reset. Once a P-wave is no longer detected, if AF criteria are still met, the ICM may then record entry to an AF episode.

Additionally or alternatively, during an ongoing AF episode, if a P-wave is detected before the AF detection process determines that the AF episode has exited, the processors may end the AF episode immediately. In the foregoing examples, the P-wave detection process is utilized as a binary "block/allow" for AF Entry and Exit determinations by an AF detection process. Additionally or alternatively, embodiments herein may utilize the P-wave detection in a non-binary manner, rather as a signal to alter a threshold utilized by the AF detection process to determine AF entry and AF exit. For example, when the processes described herein detect a P-wave in real-time, the processes may increase an AF entry or AF exit threshold (e.g., by increasing the threshold 20%) utilized by an AF detection process.

The processes of FIGS. 8A and 8B have been modeled in connection with offline or post-processing implementation. More specifically, the operations were modeled utilizing stored electrograms that were recorded in connection with an AF episode, where the electrograms extended over cardiac cycles preceding and cardiac cycles following the AF trigger. A portion of the electrograms analyzed with the model included true positive AF episodes and false positive AF episodes, with the P-wave detection process of FIGS. 8A and 8B utilized in connection with positive P-wave detection to correct one or more false-positive AF episodes.

Additionally or alternatively, the operations of FIGS. 8A and 8B may be applied on-board an ICM in real-time or near-real-time, and may be used as an integrated part of an AF determination/detection process, rather than a verification process to be applied after AF detection. When applied in an onboard real time implantation, the beat selection process of FIG. 8A would be initiated as described above once an AF detection process reaches some intermediate threshold, such that P-wave ensemble averaging may not be required for every beat, but still begins before an AF trigger. By way of example, a maximum number of beats may be defined for the P-wave segment ensemble, such as when utilizing a memory buffer of 32 beats. The beats recorded by the memory buffer need not be consecutive but rather may include only beats that fit the beat selection criteria and are less than some threshold number of beats (or time duration) in the past. For example, the buffer may hold up to 32 of the most recent beats fitting the rate based selection criteria at 804 in FIG. 8A (e.g., 600-1500 ms cycle length, and not more than +/−100 ms different from previous cycle). Additionally or alternatively, the buffer may only store beats that occurred a predetermined number of cardiac cycles prior to a current beat (e.g., no more than 64 beats prior to the current beat). As each beat is detected, if the beat meets the rate based selection criteria then the P-wave segment samples from 300 ms to 75 ms before the R-wave are added to the buffer, and any beats currently in the buffer with index greater than 64 beats prior are discarded from the buffer. The buffer may also discard any beats beyond a predetermined total (e.g., 32 beats). For example, the processors may maintain a running sum beat by beat as new P-wave segments are added to and subtracted from the buffer, rather than computing a full average every time. The remaining processing steps for P-wave detection as described above are carried out unchanged.

Optionally, amplitude information may be utilized to distinguish between P-waves and noise. For example, as described above, certain operations normalize signals before performing correlation. Normally correlations vary between +1 and −1 and it is possible that a very "noise" transition may have a correlation that is greater than 0.85. At 804, the processors may analyze the results of correlation by looking at a numerator of a correlation, sum(X*Y) without normalization by dividing by sqrt(sum(X*X)*sum(Y*Y). The amplitude information is retained. The processors may compare the sum(X*Y) to a threshold to prevent noise from masquerading as P-wave.

Closing

The various methods as illustrated in the Figures and described herein represent exemplary embodiments of methods. The methods may be implemented in software, hardware, or a combination thereof. In various of the methods, the order of the steps may be changed, and various elements may be added, reordered, combined, omitted, modified, etc. Various of the steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

Various embodiments of the present disclosure utilize at least one network that would be familiar to those skilled in the art for supporting communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C # or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also Include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements night be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

All references, including publications, patent applications and patents, cited herein are hereby incorporated by reference to the same extent as if each reference were individually and specifically indicated to be incorporated by reference and were set forth in its entirety herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and physical characteristics described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A computer implemented method for detecting arrhythmias in cardiac activity, comprising:
   under control of one or more processors configured with specific executable instructions,
   obtaining a far field cardiac activity (CA) data set that includes far field CA signals for a series of beats, the far field CA signals collected by two or more electrodes located remote from a right atrium;
   determining, based on the far field CA signals, whether a current beat satisfies a rate based selection criteria;
   declaring the current beat, from the CA signals, to be a candidate beat or an ineligible beat based on whether the current beat satisfies the rate based selection criteria;
   repeating the determining and declaring operations for multiple beats to form an ensemble of candidate beats;
   calculating a P-wave segment ensemble by combining candidate P-wave segments from the far field CA signals for the ensemble of candidate beats;
   performing a morphology-based comparison between the P-wave segment ensemble and at least one of a monophasic or biphasic template;
   declaring a valid P-wave to be present within the CA signals based on the morphology-based comparison; and
   utilizing the valid P-wave in an arrhythmia detection process to determine at least one of an arrhythmia entry, arrhythmia presence or arrhythmia exit.

2. The method of claim 1, wherein the rate based selection criteria represents a RR interval rate criteria in which a beat is disregard, as the ineligible beat, when the RR interval is outside of a predetermined range.

3. The method of claim 1, wherein the determining operation comprises applying a two-part selection test that includes i) determining whether an RR interval of the current beat is within a predetermined range and ii) determining whether the current beat is greater or shorter than a previous beat, and if shorter, determining whether the current beat has a duration that is within a range of the previous beat.

4. The method of claim 1, further comprising:
   overlaying a P-wave search window onto a candidate segment within corresponding candidate beats to obtain candidate P-wave segments;
   combining the candidate P-wave segments to form a P-wave combination; and
   determining whether a signal characteristic of interest from the P-wave combination exceeds one or more P-wave limits.

5. The method of claim 1, further comprising de-trending the ensemble of candidate beats to remove baseline drift from individual P-wave segments for corresponding candidate beats.

6. The method of claim 1, further comprising normalizing the P-wave segment ensemble before performing the correlating operation.

7. The method of claim 1, further comprising correlating a first P-wave segment, for a first beat from the ensemble of candidate beats, with the P-wave segment ensemble for the ensemble of candidate beats for morphology similarity analysis.

8. The method of claim 1, wherein the declaring operation further comprises declaring the valid P-wave to be present within the CA signals when the correlation between the P-wave segment ensemble and at least one of the monophasic or biphasic template satisfies a correlation threshold.

9. The method of claim 1, wherein the declaring operation further comprises declaring the P-wave segment ensemble to not include a P-wave when the correlation between the P-wave segment ensemble and both of the monophasic and biphasic templates do not satisfy a correlation threshold.

10. A computer implemented method for detecting arrhythmias in cardiac activity, comprising:
    under control of one or more processors configured with specific executable instructions,
    obtaining a far field cardiac activity (CA) data set that includes far field CA signals for a series of beats;
    determining whether a current beat satisfies a rate based selection criteria;
    declaring the current beat, from the CA signals, to be a candidate beat or an ineligible beat based on whether the current beat satisfies the rate based selection criteria;
    repeating the determining and declaring operations for multiple beats to form an ensemble of candidate beats;
    calculating a P-wave segment ensemble by combining candidate P-wave segments from the ensemble of candidate beats;
    performing a morphology-based comparison between the P-wave segment ensemble and at least one of a monophasic or biphasic template;
    declaring a valid P-wave to be present within the CA signals based on the morphology-based comparison;

utilizing the valid P-wave in an arrhythmia detection process to determine at least one of an arrhythmia entry, arrhythmia presence or arrhythmia exit; and truncating the candidate P-wave segments when a signal characteristic exceeds one or more P-wave limits, the calculating operation calculating a final P-wave segment ensemble based on the candidate P-wave segments after truncation.

11. A system for detecting arrhythmias in cardiac activity, comprising:

two or more electrodes configured to be located remote from a right atrium and to obtain far field cardiac activity (CA) signals;

memory to store specific executable instructions;

one or more processors configured to execute the specific executable instructions for:

obtaining a far field CA data set that includes the far field CA signals for a series of beats;

determining, based on the far field CA signals, whether a current beat satisfies a rate based selection criteria;

declaring the current beat, from the CA signals, to be a candidate beat or an ineligible beat based on whether the current beat satisfies the rate based selection criteria;

repeating the determining and declaring operations for multiple beats to form an ensemble of candidate beats;

calculating a P-wave segment ensemble by combining candidate P-wave segments from the far field CA signals for the ensemble of candidate beats;

performing a morphology-based comparison between the P-wave segment ensemble and at least one of a monophasic or biphasic template;

declaring a valid P-wave to be present within the CA signals based on the morphology-based comparison; and utilizing the valid P-wave in an arrhythmia detection process to determine at least one of an arrhythmia entry, arrhythmia presence or arrhythmia exit.

12. The system of claim 11, wherein the rate based selection criteria represents a RR interval rate criteria in which a beat is disregard, as the ineligible beat, when the RR interval is outside of a predetermined range.

13. The system of claim 11, wherein the one or more processors are configured to perform the determining operation by applying a two-part selection test that includes i) determining whether an RR interval of the current beat is within a predetermined range and ii) determining whether the current beat is greater or shorter than a previous beat, and if shorter, determining whether the current beat has a duration that is within a range of the previous beat.

14. The system of claim 11, wherein the one or more processors are configured to further:

overlay a P-wave search window onto a candidate segment within corresponding candidate beats to obtain candidate P-wave segments;

combine the candidate P-wave segments to form a P-wave combination; and determine whether a signal characteristic of interest from the P-wave combination exceeds one or more P-wave limits.

15. The system of claim 11, wherein the one or more processors are further configured to de-trend the ensemble of candidate beats to remove baseline drift from individual P-wave segments for corresponding candidate beats.

16. The system of claim 11, wherein the one or more processors are further configured to normalize the P-wave segment ensemble before performing the correlating operation.

17. The system of claim 11, wherein the one or more processors are further configured to correlate a first P-wave segment, for a first beat from the ensemble of candidate beats, with the P-wave segment ensemble for the ensemble of candidate beats for morphology similarity analysis.

18. The system of claim 11, wherein the one or more processors are further configured to declare the valid P-wave to be present within the CA signals when the correlation between the P-wave segment ensemble and at least one of the monophasic or biphasic template satisfies a correlation threshold.

19. The system of claim 11, wherein the one or more processors are further configured to declare the P-wave segment ensemble to not include a P-wave when the correlation between the P-wave segment ensemble and both of the monophasic and biphasic templates do not satisfy a correlation threshold.

20. A system for detecting arrhythmias in cardiac activity, comprising:

memory to store specific executable instructions;

one or more processors configured to execute the specific executable instructions for:

obtaining a far field cardiac activity (CA) data set that includes far field CA signals for a series of beats;

determining whether the current beat satisfies a rate based selection criteria;

declaring the current beat, from the CA signals, to be a candidate beat or an ineligible beat based on whether the current beat satisfies the rate based selection criteria;

repeating the determining and declaring operations for multiple beats to form an ensemble of candidate beats;

calculating a P-wave segment ensemble by combining candidate P-wave segments from the ensemble of candidate beats;

performing a morphology-based comparison between the P-wave segment ensemble and at least one of a monophasic or biphasic template;

declaring a valid P-wave to be present within the CA signals based on the morphology-based comparison;

utilizing the valid P-wave in an arrhythmia detection process to determine at least one of an arrhythmia entry, arrhythmia presence or arrhythmia exit; and truncating the candidate P-wave segments when a signal characteristic exceeds one or more P-wave limits, the calculating operation calculating a final P-wave segment ensemble based on the candidate P-wave segments after truncation.

* * * * *